US006495739B1

(12) United States Patent
Lassner et al.

(10) Patent No.: US 6,495,739 B1
(45) Date of Patent: *Dec. 17, 2002

(54) PLANT PHOSPHATIDIC ACID PHOSPHATASES

(75) Inventors: Michael W. Lassner, Davis, CA (US); Diane M. Ruezinsky, Woodland, CA (US)

(73) Assignee: Calgene LLC, Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/360,376

(22) Filed: Jul. 23, 1999

Related U.S. Application Data

(63) Continuation-in-part of application No. 09/122,315, filed on Jul. 24, 1998.

(51) Int. Cl.[7] .......................... A01H 5/00; C12N 15/82; C07H 21/04
(52) U.S. Cl. ..................... 800/281; 800/298; 435/419; 435/468; 536/23.6
(58) Field of Search .................... 800/281, 298; 536/23.6; 435/69.1, 468, 419, 430

(56) References Cited

FOREIGN PATENT DOCUMENTS

WO          WO 95/27791          10/1995

OTHER PUBLICATIONS

Broun et al, "Catalytic Plasticity of Fatty Acid Modification Enzymes Underlying Chemical Diversity of Plant Lipids" Nov. 1998, Science vol. 282, pp. 1315–1317.*
Van De Loo et al, "An oleate 12–hydroxylase from *Ticinus communis* L. is a fatty acyl desaturase homog", Jul. 1995, Proc. Natl. Acad. Science, vol. 92 pp. 6743–6747.*
De Luca, "Molecular characterization of secondary metabolic pathways", 1993, AgBiotech News and Information vol. 5 No. 6 pp. 225n–229N.*
Bork, "Go Hunting in sequence databases but watch out for the traps", 1996, TIG vol. 12 No. 10 pp. 425–427.*
Smith et al, The challenges of genome sequence annotation or "The devil is in the details", 1997, Nature Biotechnology vol. 15 pp. 1222–1223.*
Doerks, "Protein annotation: detective work for function prediction", 1998, TIG vol. 14 No. 6 pp. 248–250.*
Brenner, "Errors in genome annotation", 1999, vol. 15 No. 4 pp. 132–133.*
Venter et al., "The Sequence of the Human Genome" *Science*, 291:1304–1351 (Feb. 2001).
Woese et al., "Conservation of primary structure in 16S ribosomal RNA" *Nature*, 254:83–85 (Mar. 1975).
Stymne, et al., "Triacylglycerol Biosynthesis" *The Biochemistry of Plants* vol. 9 pp: 175–214 (1987).

Kai, et al., "Cloning and Characterization of Two human Isozymes of Mg2+–independent Phosphatidic Acid Phosphatase", *The Journal of Biological Chemistry* (1997) vol. 272, No. 39 pp: 24572–24578.
Kai, et al., "Identification and cDNA Cloning of 335–kDa Phosphatidic Acid Phosphatase (Type 2) Bound to Plasma Membranes" *The Journal of Biological Chemistry* (1996) vol. 271, No. 31, pp: 18931–18938.
Kanoh, et al., "Phosphatidic acid phosphatase from mammalian tissues: discovery of channel–like proteins with unexpected functions" *Biochimica et Biophysica Acta* (1997) pp: 56–62.
Katagiri, et al., Abstract: "A Role of Phosphatidic Acid Phosphatase (PAP) in Cell Elongation in Arabidopsis thaliana" Annual Meeting of The Japanese Society of Plant Physiologists, May 3–5, 1998, p. 460 Abstract XP000863412.
Sun, et al., "Acyl Coenzyme A Preference of the Glycerol Phosphate Pathway in the Microsomes from the Maturing Seeds of Palm, Maize,and Rapeseed" *Plant Physiol.* (1988) pp: 56–60,.
Lohden, et al., "Triacylglycerol biosynthesis in developing seeds of *Tropaeolum majus* L. and *Limnanthes douglasii* R. Br." Planta (1992) 188: 215–224.
Berg, et al., "Purification of a phosphatase which hydrolyzes phosphatidic acid, a key intermediate in glucolipid synthesis in *acholeplasma laidlawii* A membranes" *Biochimica et Biophysica Acta* 1330 (1997)pp: 225–232.
Carman, George M., "Phosphatidate phosphatases and diacylglycerol pyrophosphate phosphatases in *Saccharomyces cerevisiae* and *Escherichia coli* " *Biochimica et Biophysica Acta* 1348 (1997) 45–55.
Katagiri, et al., "Molecular cloning of a cDNA encoding diacylglycerol kinase (DGK) in *Arabidopsis thaliana* " *Plant Molecular Biology* 30: 647–653 (1996).
Kocsis, M. G. et al., "Phosphatidate phosphatases of mammals, yeast, and higer plants" *Lipids* 8: 785–802, (1996).
Budziszewski, G. J. et al., "Uses of biotechnology in modifying plant lipids" *Lipids* 6: 557–569, (1996).
Park, Y. et al., "Brassica EST AC H74464" EMBL Database. Nov. 3, 1995, XP002126343.
Abstract. Newman, T. et al., "Arabidopsis EST AC T88254" Apr. 1, 1995, XP002126341.
Abstract. Newman, T. et al., "Arabidopsis EST AC AA394650" Apr. 27, 1997, XP002126341.

* cited by examiner

*Primary Examiner*—Elizabeth F. McElwain
(74) *Attorney, Agent, or Firm*—Arnold & Porter; Brian K. Stierwalt

(57) ABSTRACT

By this invention, novel nucleic acid sequences encoding for phosphatidic acid phosphatase (PAP) proteins are provided, wherein PAP protein is active in the formation of diacylglycerol from phosphatidic acid. Also considered are amino acid and nucleic acid sequences obtainable from PAP nucleic acid sequences and the use of such sequences to provide transgenic host cells capable of producing altered lipid compositions and total lipid levels.

74 Claims, 18 Drawing Sheets

```
                 190        200        210        220        230        240
YEAST      DVCTTKNHERLLDGFRTTPSGHSSESFAGLGYLYFWLCGQLLTESPLMPLWRKMVAFLPL
Mouse PAP  YICQ-GNEKVKEGRLSFYSGHSS--FSMYCMLFVALYLQARMKGDWARLLRPMLQFGLI
Rat        FVCQ-GNEQKVREGRLSFYSGHSS--FSMYCMLFVALYLQARMKGDWARLLRPMLQFGLI
Human      YRCR-GDDSKVQEARKSFSGHAS--FSMYTMLYLVLYLQARFTWRGARCSGPSCSSP 250        260        270        280        290        300
YEAST      LGAALIAISRTQDYRHHFVDVIILGSMLGYIMAHFFYRRIFPPIDDPLPFKPLMD-DSDVT
Mouse PAP  AFSIYVGLSRVSDYKHHWSDVTVGLIQGAAMAILVALYVSDFFKDTHSYKERKEDPHTT
Rat        ALSIYVGLSRVSDYKHHWSDVLIGLIQGAVVAILVVLYVTDFFKTESNKERKE-DSHTT
Human 310        320        330        340        350        360
YEAST      LEEAVTHQRIPDEELHPLSDEGM
Mouse PAP  LHETASSRNYSTN--HEP
Rat        LHETTNRQSYARN--HEP
Human
```

FIG. 1b

```
CAAAAAACTTTATCTTTCCTTCCTTTGAAATCTCCCGGAGAAAAACTATAGAGA
TTTTCCGTTTCCCGCTTTAATACAGTGCCCCAATTCGCGCGACACATAGAGTGT
AGAGACGCTTTCACGAGCGTTTCCGACGTCGGACTTTCAGCTCATCATCTCCAC
ATCTTTAACGGTAAAGATTAATCATGCCTGAAATTCATTTGGGTGCTCATACAA
TAAGATCCCATGGAGTAACAGTCGCGAGGTTCCACATGCATGACTGGCTCATTC
TTCTGCTGCTAATAGTCATTGAATTGTTCTTAATGTCATCGAACCCTTTCATC
GTTTTGTTGGAGAAGATATGCTCACTGATCTCAGATACCCTCTGCAGGACAACA
CAATTCCTTTCTGGGCTGTCCCGTTGATAGCTGTTGTGCTACCTTTTGCTGTCA
TTTGTGTTTACTACTTCATTAGAAATGATGTTTATGACCTGCATCATGCAATAC
TAGGGCTTTTGTTCTCTGTACTTATAACCGGTGTCATAACCGATGCTATAAAGG
ACGCTGTTGGTCGACCTCGTCCTGATTTCTTTTGGCGTTGTTTCCCTGACGGTA
TAGGGATCTTTCACAATGTCACGAAGAATGTTCTATGTACTGGAGCTAAGGATG
TGGTCAAAGAGGGACACAAGAGCTTCCCCAGCGGCCACACATCTTGGTCGTTTG
CTGGTCTAGGATTTCTATCGTTATACTTGTCTGGGAAAATCAGGGTGTTTGACC
AGAGAGGGCATGTTGCAAAGCTCTGCATTGTGATTTTACCTCTACTGGTTGCAG
CATTGGTTGGTGTATCCAGAGTTGATGACTATTGGCATCACTGGCAAGATGTTT
TTGGAGGAGCTATCATAGGATTGACTGTGGCCACATTTTGTTATCTGCAATTTT
TCCCTCCTCCATACGATCCAGACGGTTGGGGACCTCATGCCTACTTCCAGATGC
TGGCAGACTCAAGAAATGATGTCCAAGATTCAGCAGGAATGAATCATCTAAGCG
TGAGGCAAACAGAGCTAGAGAGCGTACGTTGATGGAGAAGAGACGTCCATGGAA
ATATCAAGAAGCAACACGCGGGACACCACCCGTATGCTTCAGAACCGCTAAGTG
AAGTCTTTGTACTCGTTATCTATCAATCTTAGGCATTGTCGCATTGATATGTAT
TGGCTTAATCACAAGGCCCAATATTGGTTGGAAGCCCATTCGCT
```

```
MPEIHLGAHTIRSHGVTVARFHMHDWLILLLLIVIEIVLNVIEPFHRFVGEDML
TDLRYPLQDNTIPFWAVPLIAVVLPFAVICVYYFIRNDVYDLHHAILGLLFSVL
ITGVITDAIKDAVGRPRPDFFWRCFPDGIGIFHNVTKNVLCTGAKDVVKEGHKS
FPSGHTSWSFAGLGFLSLYLSGKIRVFDQRGHVAKLCIVILPLLVAALVGVSRV
DDYWHHWQDVFGGAIIGLTVATFCYLQFFPPPYDPDGWGPHAYFQMLADSRNDV
QDSAGMNHLSVRQTELESVR
```

FIG. 2

```
CCCACGCGTCCGCCACATTTCTCTTTAACCTCATCTCATCTCTTAGTCGAGATC
TTCACTTTCTGATGACAATAGGGTCGTTTTTCTCTTCTCTCTTATTCTGGCGCA
ATTCTCAGGACCAGGAGGCGCAGAGAGGGAGGATGCAGGAGATAGATCTTAGTG
TTCACACTATAAAGTCCCATGGAGGAAGAGTCGCTTCTAAACACAAGCACGATT
GGATCATACTCGTCATCTTGATTGCCATCGAGATAGGCTTGAACCTCATCTCTC
CTTTCTACCGCTACGTGGGAAAAGACATGATGACTGACCTCAAGTACCCTTTCA
AGGACAACACCGTACCTATCTGGTCTGTCCCTGTGTACGCTGTGCTTCTTCCCA
TCATAGTGTTCGTCTGCTTCTACCTGAAGAGGACATGTGTGTACGATCTGCACC
ACAGCATCCTCGGGCTGCTCTTCGCCGTCTTGATAACTGGTGTCATCACTGACT
CCATCAAGGTAGCCACCGGACGCCCTCGTCCTAACTTCTACTGGCGCTGCTTCC
CCGACGGCAAGGAGCTGTATGATGCGTTGGGAGGTGTGGTATGCCACGGCAAGG
CAGCTGAGGTCAAGGAAGGCCACAAGAGCTTCCCGAGCGGACACACTTCCTGGT
CCTTTGCGGGGCTTACATTCCTTTCCCTTTACCTCTCTGGCAAAATCAAGGCCT
TCAACAATGAAGGACATGTGGCGAAACTCTGCCTCGTGATCTTCCCTCTGCTTG
CCGCTTGTCTTGTGGGGATATCTCGTGTGGATGACTACTGGCACCACTGGCAAG
ATGTCTTCGCAGGAGCTCTCATTGGCACCCTTGTAGCCGCCTTCTGCTACCGTC
AGTTCTACCCCAACCCTTACCACGAAGAAGGATGGGGTCCCTACGCCTATTTCA
AGGCAGCTCAAGAACGAGGAGTCCCTGTGACCTCCTCCCAAAACGGAGATGCCT
TGAGGGCTATGTCTCTGCAGATGGATTCAACATCTCTCGAAAACATGGAATCTG
GCACTTCCACCGCTCCCAGATGATCCTCCTCTCTTATTATTTGATTCATTATTT
GGTTTTTCATTTTGATTTGGCCGTCGTCGTGAGATTGTGAATGGTGTAGCTACA
TACTGTATGTGTATTCAAAACTCTACTTGTACCATTACATTTTTGTAAATCCAC
TCTTCATGAAATTGACGTTAAAAAAAAAAAAAAA

HASATFLFNLISSLSRDLHFLMTIGSFFSSLLFWRNSQDQEAQRGRMQEIDLSV
HTIKSHGGRVASKHKHDWIILVILIAIEIGLNLISPFYRYVGKDMMTDLKYPFK
DNTVPIWSVPVYAVLLPIIVFVCFYLKRTCVYDLHHSILGLLFAVLITGVITDS
IKVATGRPRPNFYWRCFPDGKELYDALGGVVCHGKAAEVKEGHKSFPSGHTSWS
FAGLTFLSLYLSGKIKAFNNEGHVAKLCLVIFPLLAACLVGISRVDDYWHHWQD
VFAGALIGTLVAAFCYRQFYPNPYHEEGWGPYAYFKAAQERGVPVTSSQNGDAL
RAMSLQMDSTSLENMESGTSTAPR
```

FIG. 3

GCGTCCGATCGACTAGAGTCTGCACAGGATGAGAGAGGCACAGCTAGGCGGTCA
CACTCTGAGGTCCCATGGAATGACTGTTGCAAGGACTCACATGCATGATTGGAT
CATTCTCGTGTTACTTGTTATTCTCGAGTGTGTACTCCTTATAATCCACCCATT
TTATCGCTTTGTTGGTAAAGATATGATGACTGATCTAAGTTACCCGTTAAAGAG
TAACACCGTACCAATTTGGTCTGTCCCGGTATATGCGATGCTGTTACCTTTGGT
AATCTTCATCTTTATCTACTTCCGTCGAAGAGATGTTTATGATCTTCATCACGC
GGTGCTAGGTCTCTTATACTCTGTTCTGGTGACAGCAGTACTTACCGATGCAAT
AAAGAATGCAGTTGGTCGACCACGTCCTGACTTCTTCTGGCGTTGTTTTCCAGA
TGGCAAAGCTCTTTATGATAGCCTTGGAGATGTTATGCCATGGTGATAAAAG
CGTCATAAGGGAAGGTCACAAAAGCTTTCCAAGTGGACACACGTCATGGTCTTT
TTCGGGTCTCGGATTTCTTTCGCTTTACTTATCGGGAAGATTCAAGCATTTGA
CGGTAAAGGCCACGTTGCAAAGCTATGCATAGTCATACTCCCTTTGCTATTTGC
AGCTCTTGTCGGCATTTCCCGTGTTGATGACTATTGGCATCATTGGCAAGACGT
CTTTGCAGGAGGCTTGCTAGGTCTTGCGATCTCTACAATCTGTTATCTTCAATT
TTTCCCGCCACCATATCACACCGAAGGTTGGGGACCATATGCTTACTTCCAAGT
GTTGGAGGCTGCGAGAGTGCAAGGAGCAGCGAATGGAGCAGTGCAGCAGCCGCC
GCCCCAAGTTAACAACGGTGAAGAAGAAGACGGTGGGTTTATGGGTTTACATTT
GGTGGATAATCCGACTATGAGGAGAGAAGAGGATGTAGAAACTGGTAGAGGCTG
AGATGAAGAAACTCTGAAGCTGGTTTGGTTACTTGTTAGGACACTTTCTCTTGT
TCTTTTGATTCTTTGTTGGACAACTTTAGTAGATTTCTCTAAGATAACTAATAG
AGTCGTTTGGTTTTAAAAAAAAAAAAAAAAAAA

MREAQLGGHTLRSHGMTVARTHMHDWIILVLLVILECVLLIIHPFYRFVGKDMM
TDLSYPLKSNTVPIWSVPVYAMLLPLVIFIFIYFRRRDVYDLHHAVLGLLYSVL
VTAVLTDAIKNAVGRPRPDFFWRCFPDGKALYDSLGDVICHGDKSVIREGHKSF
PSGHTSWSFSGLGFLSLYLSGKIQAFDGKGHVAKLCIVILPLLFAALVGISRVD
DYWHHWQDVFAGGLLGLAISTICYLQFFPPPYHTEGWGPYAYFQVLEAARVQGA
ANGAVQQPPPQVNNGEEEDGGFMGLHLVDNPTMRREEDVETGRG

*FIG. 4*

```
TGATATGCCATGGTGATAAAAGTGTCATAAGTGAAGGGCACAAAAGCTTCCCAA
GCGGACACACCTCTTGGTCTTTTGCGGGTCTAGGATTCTTGTCGCTGTATTTAT
CAGGGAAGATTCAAGCGTTTCATGGTAAAGGCCACGTTGCGAACGTATGCATTG
TCATACTCCCTTTGCATGTTGCAGCTCTTGTCGGATTTCCGTGTAGATGACTAT
GGCATTCACTGGCAGACGCTTTGCTGGAGGCTGCTAGG
```

FIG. 5

```
GTCGACCCACGCGTCCGCCCACGCGTCCGCGGACGCGTGGGCGCTAGCAGCGGC
GGCGCCGGCAGTTGGTAGCCGCGACCGAGACACGGCGGGTGACCTGCCCCGCCG
CAGTCGGGGTGTATGTATTACCACCGCCAGAATTCCAGGAGACAATGGCAGACC
AGTTAGGGTCTTACACTATTAGATCCCATGGAATGATATTGGCAAGGTTGCACA
TGTATGACTGGATAATACTTCTCCTCCTTGCTGTCATAGACGGGCTGTTAATA
TAATTGAACCATTTCACCGTTTTGTTGGGAAAGACATGATGACTGACTTGAGAT
ATCCTATGAAGGGCAATACAGTGCCATTTTGGGCTGTTCCACTGATTGGAATTA
TACTGCCTTGGGCCATCTTTGTTGGGATTTACTTCAAAAAGAAGAATTTTTATG
ATTTGCACCATGGCATACTGGGGATTCTATACTCAGTGCTGATAACTGCAGTGA
TTACTGATGCAATTAAGGATGGTGTTGGACGGCCTCGTCCAGATTTTTTCTGGC
GCTGTTTCCCTAATGGAAATGATGTTTATGATAACATTACTACTGGTGTTATAT
GCAATGGAGTGAAGAGCGTAATCAAGGAAGGCCACAAGAGCTTTCCCAGTGGAC
ACAGTTCATGGTCTTTTGCTGGTCTAGGCTTCCTTGCATGGTACTTAGCTGGGA
AACTCACAGCCTTTGACCGCAAAGGGCATATTGCGAAGCTATGCATTGTGTTCC
TGCCTCTCCTTACTGCCGCACTTGTGGCTGTTTCTCGAGTGGACGACTACTGGC
ATCATTGGCAAGATGTATTTGCAGGGGGTCTTATAGGTCTTACAGTTGCTTCGT
TTTGCTACCTACAGTTTTTCCCATATCCTTTCGATGGCGATGCTTTGTGGCCTC
ACGCATACGCGGTCCGGTTAGCCGAGGAGGGGAACAGCAGAAATGCGAACTCGT
ACAGCGTGAGACCAACCGAGATCGAAACAGTCGATATTCCTGGGCACGGTGCGA
TCATCACCCTAAGAGAGACTCTAAACGATGTGGAGTCTGGCAGTGCCAGGAGAT
TGTGAGATGGGTCTGCAGGTGTGGAGATTGATGTCTCAGATACCATGGGAGTTG
CTTGCATATGTGTACAGGTAGATCTATTGTAGAGCTGTTGACTGCTGCCACCGT
GATAGGGGAGGGTTGCTTAGACGGGCCTGGCAGTAAATTTACTTGGTAGGGGTG
CTGTTTCTTCTGAGAACCTTTGGCTTTTGTTTGTATATATACTCTTATCAAAGT
GTTTGCTGACACTTTTGTAACCAGTTTGGTCGCTGCATTCAGCAACTATGATCA
AAAAAAAAAAAAAAAAAAAAAAAAAAAGGGCGGCCGC

MADQLGSYTIRSHGMILARLHMYDWIILLLLAVIDGLLNIIEPFHRFVGKDMMT
DLRYPMKGNTVPFWAVPLIGIILPWAIFVGIYFKKKNFYDLHHGILGILYSVLI
TAVITDAIKDGVGRPRPDFFWRCFPNGNDVYDNITTGVICNGVKSVIKEGHKSF
PSGHSSWSFAGLGFLAWYLAGKLTAFDRKGHIAKLCIVFLPLLTAALVAVSRVD
DYWHHWQDVFAGGLIGLTVASFCYLQFFPYPFDGDALWPHAYAVRLAEEGNSRN
ANSYSVRPTEIETVDIPGHGAIITLRETLNDVESGSARRL
```

FIG. 6

CTCGAGTTGATATTCCCAATCTCTCTGTTTCTATTTCTTTGTTCGTTGCTTCAC
ACTATGGCTTCTTGGTGGGATTTAAGACCCTTCTTTCGTTTTCAGTCTGTTAGG
ACCCGATTTCAGGAATTCAGGACGAGGGAAGTCCAACTTGGTTCACATACTGTG
AGTTCTCATGGATATGCAGTTGCAAGAACACACAAACATGATTGGCTCATTCTC
TTGCTCCTCGTGTTGATTGTTATC
AGCCTGTACATTATCCATCCTTTCCATCGCTTTGTTGGGAAGGATATGATGACT
GATCTCAAATATCCACTGAAGAGTAATACAGTTCCTGCTTGGGCTATTCCTATA
TATGCAATTTTATTGCCCATAGTGATCTTTCTTGGTGTCTACATCCGAAGGAGA
GACGTCTATGATCTTCATCATGCTGTGCTGGGTTTATTGTTCTCCGTTTTAATA
ACAGCAGTATTTACTGAGGCAATA
AAAAATGCAGTAGGTCGACCTCGACCAGACTTCTTCTGGCGATGTTTTCCAGAT
GGAAAGGATGTTTATGATAAATGGGGAGATGTCATTTGTCATGGTGACCAAAAG
GTCATAAAGGAAGGATACAAGAGTTTCCCAAGTGGTCATACTTCAGGGTCATTT
TCTGGTCTGGGTTTTTTATCATTGTACTTATCTGGAAAAATAAAAGCATTTGAT
CGCAAAGGTCATGTTGCAAAACTT
TGCATTGTTTTTCTACCACTACTTGTTGCATCACTTGTTGGCATTTCTCGAGTT
GATGACTACTGGCACCACTGGCAAGACGTGTTTGCGGGAGGTCTTTTAGGGCTT
ACAGTGGCTACATTTTGCTATTTGCAGTTTTTTCCTCCTCCTTATCATTCTGAA
GGCTGGGGTCCTTATGCGTATTTTAGGATGTTGGAAGAATCTCGTGGTATGACC
CAAGTTCCTAGTGTTCAAAATTCT
GGTCAAGCGCAGTTAGCAGAGGCTCAGGCTGAGAGCCAAGAGGAACAAGGTCTC
CACGGGTGTATGGGGTTAACTTTATCACGGGATCATCATGCAGCATTGAATGAC
TGTGAATCTGGGAGGGGATAAAGTCTGTACATTTCATGATCTTGCTCTCTGTAA
AATGTAAATCAGATGTTAGTTCGTAGCCTAGGATTTTAACCAGTATTTAAAACT
AACACATTTTGTTGAATAGTTGTT
TCTATTCAGTCACTAGTGTCTCTGAAAACTTTGAAGCGTAGTTGTTTGTAAGAG
TCAGGTTTGGGACAATTAACCTTTGTTATTTCAATATTTTGTGAATATGTTGAC
ATAAGAAAATACGAAATCTCTTGAGAAGATTGCCGTTCATTCAAAAAAAAAAAA
AA

MPEIQLGMHTIRSHGTRVARTHMHDWLILLLLVIIDAVLNLIQPFHRFVGEGMM
TDLRYPLKANTIPFWAVPIIAILLPLAVFLVYYFIRKDVYDLHHAIMGLLFSVL
ITAVMTDAIKDAVGRPRPDFFWRCFPDGKGVFDPVTSNVLCTGDKGVIKEGHKS
FPSGHTSWSFAGLVYLAWYLSGKLRAFDRRGHVAKLCLVFLPILVAAMIAVSRV
DDYWHHWQDVFAGALIGMIIASFCYLQFFPPPYDVDGWGPHAYFQMLAESRNGA
QPSTVNNEIHHVQSAELQAVSLYIPPQHDADTRGNSWDSSPMLGASQNVRTH

FIG. 7

```
CTCGAGCCTCGAATCTCGTGCACGTGCCGTTGCAGCAAAAAATGCCAGAAATTC
AGTTGGGTATGCATACTATCAGATCACATGGAACTAGAGTGGCAAGGACACATA
TGCACGACTGGTTGATTCTTTTGCTTCTTGTGATCATCGATGCTGTCTTGAATT
TAATACAGCCATTTCACCGTTTTGTTGGAGAGGGGATGATGACAGACCTTAGAT
ACCCATTGAAAGCTAATACAATTC
CCTTTTGGGCTGTTCCGATAATAGCAATATTGTTACCACTGGCTGTTTTCTCG
TTTACTATTTCATTCGTAAGGATGTCTATGACCTCCACCATGCTATAATGGGCC
TTCTATTTTCTGTACTCATTACTGCGGTGATGACTGATGCTATCAAGGATGCTG
TTGGACGGCCAAGGCCAGACTTCTTCTGGCGTTGTTTCCTGATGGAAAAGGGG
TGTTTGATCCAGTAACAAGTAATG
TTCTGTGTACTGGAGATAAGGGTGTTATTAAGGAAGGGCACAAAAGTTTCCCCA
GTGGACATACCTCTTGGTCCTTTGCTGGTCTTGTTTATCTTGCTTGGTATCTAT
CTGGAAAACTTAGGGCATTTGACCGCAGGGGGCATGTTGCAAAGCTCTGTCTTG
TTTTCTTACCAATCCTCGTGGCAGCTATGATTGCTGTCTCTCGTGTTGATGATT
ACTGGCATCATTGGCAAGATGTGT
TTGCTGGAGCTCTTATAGGGATGATAATTGCTTCATTTGTTACTTACAATTCT
TTCCACCTCCATATGACGTAGATGGTTGGGGACCTCATGCATATTTCCAGATGT
TGGCTGAATCTCGTAATGGTGCTCAGCCCTCTACTGTCAATAATGAGATTCATC
ATGTCCAATCTGCTGAGCTTCAGGCTGTATCTTTGTATATCCCACCTCAACATG
ATGCAGATACACGAGGCAATAGCT
GGGATTCAAGCCCCATGTTAGGTGCATCCAAAATGTAAGAACACACTGACGAC
ATAGGAAAGATCACCAACATGTCCATAATCTGTAAAATTATAGGAGGGATTCG
TTGCAGATAAACCACTTTAGCATTGTTGGTGGTTTAAAATGCGGATATCAATCA
ATTTCTTTGCTTGTTGGATTGGAAATTTGGGATGCCATGTTAGTTGTCTTTAAT
TTTCCGGCCAGCTTATATTTGTTA
GTTGTCAAAGCACTGTTTCTATACAGAGAATGATTTAATCGGCTCAACAGGATT
CAAGCAAAAAAAAAAAAAAAAA
```

```
MASWWDLRPFFRFQSVRTRFQEFRTREVQLGSHTVSSHGYAVARTHKHDWLILL
LLVLIVISLYIIHPFHRFVGKDMMTDLKYPLKSNTVPAWAIPIYAILLPIVIFL
GVYIRRRDVYDLHHAVLGLLFSVLITAVFTEAIKNAVGRPRPDFFWRCFPDGKD
VYDKWGDVICHGDQKVIKEGYKSFPSGHTSGSFSGLGFLSLYLSGKIKAFDRKG
HVAKLCIVFLPLLVASLVGISRVDDYWHHWQDVFAGGLLGLTVATFCYLQFFPP
PYHSEGWGPYAYFRMLEESRGMTQVPSVQNSGQAQLAEAQAESQEEQGLHGCMG
LTLSRDHHAALNDCESGRG
```

FIG. 8

>700046467
CTCAGTGCTCATAACTGCAGTGATTACTGATGCAATAAGGATGGTGTTGGACGGCCTCGTCCAGATT
TTTCTGGCGCT
GTTCCCTGATGGAAATGATGTTTATGATAACATCACTACTGGTGTTATATGCAATGGAGTGAAGAGT
GTAATCAAGGAA
GGCCACAAGAGCTTCCCAGTGGACACACTTCATGCTCCTTGCATGGTACTTAGCTGGGANACTCAC
GGCTTTTGATCG
NAAAGGACCTATTGCGAACTATGCATT
>700050949
ACCGACTTGAGTTATCCCCTCAAGGGCAACACAATCCCATTTGGGCTGTCCACTGATTGCGATCGT
GCTACCCTTGGT
TATCTTTGCTGTCATTACTTCAAAAAGAAAAATGTCTATGATTACACCACGGCATACTAGGTATCTT
GTATTCAGTGC
TTATAACTGCTGTGATCACTGATGCAATTAAGGATGGTGTTGGTGTCGCCCTGGCCCTGCCCAGATTTCTTTGGC
GTTGTTTCCT
GATGGCAAACCTAATTTTAATAATATAACCCACCGATGTGATATGGCCATGGA
>700105029
CGCTTAGCAGCGGCGGGCGCCGGCCGGCAGTGGTAGCCGGACCGGAGACACGGCGGGTGACCTGCCCCGNC
GCAGTCGGGGTGN
ATGTANTACCANCGCCAGAATANCAGGAGACAATGGCAGACCAGTTAGGGTCTTACACTATTAGATC
CCATGGAATGATA
TGGCAAGGTTGCACATGTATGACTGGATAATACTTCTCCCTGCTGTCATAGAGCGGGCTGTTGAA
TATAATTGAACC
ATTTCACCGTTTTGTTGGGAAAGACATGATGACTGACTTGAGATATCC

*FIG. 10a*

```
>700159470
CTTAGTGGCAGTTTCTCGAGTGATGACTATTGGCATCATTGGCAAGACGTATGTACTGGCGGATTAC
TTGGGTTCACGG
TTGCTTCCATTTGCTACCTGCAGTTTTTCCACTACCATCTGATGAAAATGGACTGTGGCCACGCAT
ATTCCGACAC
ATTCTTGAGCCAAGAGGGTGACAGAGGCAAGCCAAGCCAACCCACGTACACATGAGCCGTCGCAGCTCGGTTCAGA
>700172426
TGCTGTGTCATAGAACGGGGCTGTTGAATATAATTGAACCATTTCACCGTTTGTTGTGGGAAAGACATGATGA
CTGACTTGAGAT
ATCCTATGAAGGGCAATACAGTGCCATTTGGGCTGTTCCACTGATGGAATTATACTGCCTTGGGCC
ATCTTTGTGGG
ATTTACTTCAAAAAGAAGAATTTTTATGATTGCACCATGGCATACTGGGGATTCTATACTC
>700185072
CACAGCCTTTGACCGCAAGGGCATATTGCCAAGGAATTATTGCATTGTGTTCCTGCCTCTCCNNNCTGCNG
CACTTGTGGCTG
TTATCTCGAGTGGACGACTACTGGCATCATTGGCAAGATGTATTGCAGGGGGTCTTATAGGTCTTAC
AGTTGCTTCGTT
TTGCTACCTACAGTTTTTCCCATATCCTTTCGATGGGCGATGCTTTGTGTGGCCTCACGCATACGCGGTCCG
GTTA
```

*FIG. 10b*

>700240043
ATTAAGGATGGTGTGGACGGCCTCGTCCAGATTTTTCTGGCGCTGTTCCCTAATGAAATGATGTT
TATGATAACAT
TACTACTGGTGTTATATGCAATGGAGTGAAGAGCGTAATCAAGGAAGGCCACAAGAGCTTCCCAGT
GGACACAGTTCAT
GGTCTTTTGCTGGTCTAGGCTTCCTTGCATGGTACTTAGCTGGGAAACTCACAGCCTTTGACCGCAAA
GGGCATATTGCG
AANTATGCATTGTGTCCT
>700241109
CCCAGTGGACACAGTTCATGGTCTTTTGCTGGTCTAGGCTTCCTTGCATGGTACTTAGCTGGGAAACT
CACAGCCTTTGA
CCGCAAAGGGCATATTGCGAACTATGCATTGTGTTCCTTACTGCCCTCCTTACTGCCGCCACTGTGTGGCTGTT
TCTCGAGTGGA
CGACTACTGGCATCATTGGCAAGATGTATTGCAGGGGTCTTATAGGTCTTACAGTTGCTTCGTTTG
CTACCTACAGT
TTTTCCCATATCCCTTTCGATGG
>700242780
AACTGCAGTGATGATTACTGATGCAATTAAGGATGGTGTTGGACGGCCTCGTCCAGATTTTTCTGGCGCT
GTTCCCTAATG
GAAATGATGTTTATGATAACATTACTACTGGTGTTATATGCAATGGAGTGAAGAGCGTAATCAAGGA
AGGCCACAAGAGC
TTCCCAGTGGACACAGTTCATGGTCTTTTGCTGGTCTAGGCTTCCTTGCATGGTACTTAGCTGGGAAA
CTCACAGCCTT
TGACCGCAAAGGGCAT

*FIG. 10c*

>700428034
GATAACTGCAGTGATTACTGATGCAATTAAGGATGGTGTGGACGGCCTCGTCCAGATTTTCTGGC
GCTGTTCCCTA
ATGGAAATGATGTTTATGATAACATTACTACTGGTGTTATATGCAATGGAGTGAAGAGCGTAATCAA
GGAAGGCCACAAG
AGCTTCCCAGTGGACACAGTTCATGGTCTTTGCTGCTCTAGGCTCCTTGCATGGTACTTAGCTGGG
AAACTCACAGCC
TTGNACCGCAAAGGGCATATGCGAANTATGCATGTGTTCCTGCCCTCC
>700449914
CNTTGNNGGGCANCCCGGCAGNNACCNANGTTNNACNNGACGCGGCTGCCGTACGTGCCCTCGNTA
TGCTCTGCGTGTT
GCTGGCTGGANTGCCTTTGTAATTCTTACTTCAAGGCATACCCNCTTCCAACGANGAGTATTCTGNA
ATGNTGAGTCCN
TCANGTACCCTTACAAAGAAGACACNATNCCTTATGCGGTTATTAGGTGGNATNATCANNCCATTCAG
GATTATCGGTATT
ANNCGTGGNGNAACCTGTCCGTATATGTAACC
>700466226
GAAGGCCACAAGAGCTTCCCAGTGGACACACTTCATGGTCTTTGCTGCTAGGCTTCCTTGCATG
GTACTTAGCTGG
GAAACTCACGGCTTTGATCGCAAAGGACATATTCGGAAGCTATGCATTGTGTTCTCGCCTCTCTTA
CTGCTGCGCTTG
TGGCTGTTTCTGAGTGGATGACTACTGGCATCATTGGCAAGATGTATTGCAGGGGTCTATAGGT
CTTACAGTTGCT
TCATTTGCTATCTACAGTTTTTCCATATCCTTTGATGGCGAGCTTGTGGCCTC

*FIG. 10d*

>700467083
GAAGGCCACAAGAGCTTCCCAGTGGACACACTTCATGGTCTTATGCTGGTCTAGGCTTCCTTGCATG
GTACTTAGCTNG
GAAACTCACGGCTTTTGATCGCAAAGGACATATTCGGAAGCTATGCATTGTGATTNTGCCTCTCTTA
CTGCTGCGCTTG
TGGCTNNTTCTCGAGTGGATGACTGGCATCATGGCAAGATGTATTACAGGGGTCTTATAGGT
CTTAANTTGCTT
CATGGTGCTATCTACAGTNTTCCATATCCTTTGATGGCGATGCTTTG
>700467826
GAAGGCCACAAGAGCTTCCCAGTGGACACACTTCATGGTCTTTGCTGGTCTAGGCTTCCTTGCATG
GTACTTAGCTGG
GAAACTCACGGCTTTGATCGCAAAGGACATATTCGGAAGCTATGCATTGTGTTTCGCCTCTCTTA
CTGCTGCGCTTG
TGGCTGTGTTCTCGAGTGGATGACTACTGGCAAGATGTATTGCAGGGGTCTATAGGT
CTTACAGTTGCT
TCATTTGCNGNGNNCTACAGTTTTTCCATATCCTTTGATGGC
>700472692
GNAGGCCACAAGAGCTTTCCCAGTGGNNACACTTCATGGTCTTTTGCTGGTCTAGGCTTCCTTGCATG
GNACTTAGCTGG
GATNCTCACGGCTTTGANCGCAAAGGACTATCATTGTTTCGNCTCTCTCTTACT
GCTGCGCTTGT
GGCNGTTNCTCGAGTNGNTGACTACTGGCATCNTGGCAAGATGTANTTCCANGGGGTCTNATANGN
CTANAGTTGCTTC
ANTCTGNTANCTACAGTTNTNTCCATATCCNTNTGATGG

FIG. 10e

>700571736
GGACATGTTGCAAAAGTCTGCATTGTCCTTCCCCTCTGCTTCTTGCAGCCTTAGTGGCAGTTTCTGA
GTTGATGACTA
TTGGCATCATTGGCAAGACGTATGTACTGGCGATTACTGGGGTCACGGTTGCTTCCATTTGCTACCT
GCAGTTTTTT
CCACTACCATCTGATGAAAATGGACTGTGGCCGCACGCATATTCCGACACACATTCTTGAGCCAGAGG
GTGACAGCCAAGC
GCAACCCACGTACATGAGCCGTCGCAGCTCGGTTCAGAACGGTTCCTTCAGTAC
>700573361
CTACTGGTGTTGTTATATGCAATGAATGGAGTGAAGAGCGTAATCAAGGAAGGCCACAAGAGCTTCCCANTGG
ACACAGTTCATGG
TCTTTTGCGCTGGTTCTAGGCTTCCTTGCATGGTACTTAGCTGGGAANCTCACAGCCTTTGACCGCAAAGG
GCATATTGCGAA
NTATGCATTGTGTTCCTGCCTCCCTTACTGCCGCACTTGTGGCTGTTTCTCGAGTGGACGACTACTGG
CATCATTGGCA
AGATGTATTGCAGGGGTCTTATAGGTCTTACACAGTTCGTTGCTTGCTACCTACAGTTTTTCCCATA
TCCTTNTCGAT
GGCGATGCTTTGTGGCCTCACGCAA

*FIG. 10f*

>700577347
TGCNCCTNCCTCCTCCTCCTTACTGCCGCACTTGTGTGNCGACTACTGANCATCATTG
NTCAATATGTA
NGATGCAGGGGGTCGTATACGTCTTACAGTGTTGCTTCGTTNNGCTACCTANAGTGTNTCCCATATCCTC
TNGATGGCGATG
NTTNGTNGNCTNANGCATACNCGGTCGGTNNGCCGAGGATGGGAACAGNAGTAATGCGAACTCGTA
CAGCGTNANACCN
NCCNAGATCTATNACAGTNG
>700582565
GTGGCTGNTTCTCGAGTGATGATTACTGGCATCACTGGCAAGANGTCTATGCCGGCGATCATAGGN
CTAACAGTNGCT
TCATTCTGTTACCTGCAGTTCTCCCTTGACAATGATGCCCTATGGCCACACGCATACTNC
TCNAAGCTAGC
TGAGACACAGTAATGGTAATGCAAACTCAATCAACATAAGACCTACAGAGTNTGAAGATGAACCA
GATGACCATGGTG
CATTTTCCTGAGGGACACCAGCCCTATCTTGGAGTCAATGGAGTCTGGCAGGAGACCATGAAGNNN
NNT
>700611044
AATTCCAGGAGACGACGAGGCGCCGATCCGTAGCGCCGAGGGCCGATATCGAGGAGCCGCTGGT
CTCACGCCCGCACCG
AGACAATGGCAGACCAGTTAGGGTCTTACACAATTAGATCCCATGGAATGATATTGGCAAGATTACA
CATGTATGACTGG
ATAATACTTCTCCTCCTTGCTGTCATAGACGGGCTGTTGAATATAATTGAACCATTTCACCGTTTGTT
GGAAAAGACAT
GATGACCGACTTGAGATATCCTATGAAGGGCAATA

*FIG. 10g*

GCTTGGGGACCATATGCTTACTTCCTTGTGTTGGAGGCGGCACGA
GCTCAAGCTCAAGCTCAAGCTCAAGCTCAAGCAGCAGAGAATGA
AGCGGCCCAACGACCGCCTCAGGGTGATAACGGTGAAGAGGAAG
ACGGTGGGTTTATGGGACTACATTTGGTGGATAATCCGAGTATGA
GGAGAGAAGAAGCAGATGTAGAAGCTGGTAGAGTGCCGTCTAAA
AGCTGAGATTATAAAGAATCACTGAAGCTGGTTTGGTTGCAGCTT
AAGACACTTTTGCCTTGTTCTTATACATTCTTTTGTTTGCCTACTTG
TCCTTTGGTGTTTGGTTTACAGTTTAATGCCTTTAATTTGTTCAATT
CAGTTTTGTTCAAAAAAAAAAAAGAGGGAAAGGAGAAGGAGA
GAG

FIG. 11

PLANT PHOSPHATIDIC ACID PHOSPHATASES

This application is a continuation-in-part of application Ser. No. 09/122,315 filed Jul. 24, 1998.

TECHNICAL FIELD

The present invention is directed to nucleic acid and amino acid sequences and constructs, and methods related thereto.

BACKGROUND

Through the development of plant genetic engineering techniques, it is possible to produce a transgenic variety of plant species to provide plants which have novel and desirable characteristics. For example, it is now possible to genetically engineer plants for tolerance to environmental stresses, such as resistance to pathogens and tolerance to herbicides. Another important example for such plant genetic engineering techniques is the production of valuable products in plant tissues, such as improved fatty acid compositions.

There is a need for improved means to obtain or manipulate fatty acid compositions and content, from biosynthetic or natural plant sources. For example, novel oil products, improved sources of synthetic triacylglycerols (triglycerides), alternative sources of commercial oils, such as tropical oils (i.e., palm kernel and coconut oils), and plant oils found in trace amounts from natural sources are desired for a variety of industrial and food uses.

To this end, the triacylglycerol (TAG) biosynthesis system in mammalian tissues, yeast and plants has been studied. In the cytoplasmic membranes of plant seed tissues which accumulate storage triglycerides ("oil"), fatty acyl groups are added sequentially by specific acyltransferase enzymes to the sn-1, sn-2 and sn-3 positions of glycerol-3-phosphate (G3P) to form TAG. This pathway is commonly referred to as the Kennedy or G3P pathway (FIG. 9).

The first step in TAG formation is the acylation of the sn-1 position of glycerol-3-phosphate (G-3P), catalyzed by glycerophosphate acyltransferase (GPAT), to form lysophosphatidic acid (LA). The lysophosphatidic acid is subsequently acylated at the sn-2 position by lysophosphatidic acid acyltransferase (LPAAT) to create phosphatidic acid.

A key step in the formation of TAG is the dephosphorylation of the sn-3 position of phosphatidic acid (PA) to form sn-1,2-diacylglycerol (DAG) and inorganic phosphate catalyzed by the enzyme phosphatidic acid phosphatase (PAP, EC 3.1.3.4). The sn-1,2-diacylglycerol is acylated at the sn-3 position by diacylglycerol acyltransferase ultimately forming triacylglycerol (TAG).

The characterization of phosphatidic acid phosphatase (also known as PAP) from plants is useful for the further study of plant fatty acid synthesis systems and for the development of novel and/or alternative oils sources. Studies of plant mechanisms may provide means to further enhance, control, modify, or otherwise alter the total fatty acyl composition of triglycerides and oils. Furthermore, the elucidation of the factor(s) critical to the natural production of triglycerides in plants is desired, including the purification of such factors and the characterization of element(s) and/or cofactors which enhance the efficiency of the system. Of particular interest are the nucleic acid sequences of genes encoding proteins which may be useful for applications in genetic engineering.

SUMMARY OF THE INVENTION

The present invention provides nucleic acid sequences encoding for proteins which catalyze the dephosphorylation of phosphatidic acid (PA) to form sn-1,2-diacylglycerol (DAG). Such proteins are referred to herein as phosphatidic acid phosphatase (EC 3.1.3.4) or PAP.

By this invention, nucleic acid sequences encoding plant PAP may now be characterized with respect to enzyme activity. In particular, isolation of nucleic acid sequences encoding for PAP from Arabidopsis, Brassica, soybean and corn are provided.

Thus, this invention encompasses plant PAP nucleic acid sequences and the corresponding amino acid sequences, and the use of these nucleic acid sequences in the preparation of oligonucleotides containing PAP encoding sequences for analysis and recovery of plant PAP gene sequences. The plant PAP encoding sequence may encode a complete or partial sequence depending upon the intended use. All or a portion of the genomic sequence, or cDNA sequence, is intended.

Of special interest are recombinant DNA constructs which provide for transcription or transcription and translation (expression) of the plant PAP sequences. In particular, constructs which are capable of transcription or transcription and translation in plant host cells are preferred. For some applications a reduction in plant PAP may be desired. Thus, recombinant constructs may be designed having the plant PAP sequences in a reverse orientation for expression of an anti-sense sequence or use of co-suppression, also known as "transwitch", constructs may be useful. Such constructs may contain a variety of regulatory regions including transcriptional initiation regions obtained from genes preferentially expressed in plant seed tissue. For some uses, it may be desired to use the transcriptional and translational initiation regions of the PAP gene either with the PAP encoding sequence or to direct the transcription and translation of a heterologous sequence.

In yet a different aspect, this invention relates to a method for producing a plant PAP in a host cell or progeny thereof via the expression of a construct in the cell. Cells containing a plant PAP as a result of the production of the plant PAP encoding sequence are also contemplated herein.

In addition, methods for increasing oil content in developing seed as well as methods for producing novel oil compositions in developing seeds of oil producing plants are contemplated.

Also considered in this invention are the modified plants, seeds and oils obtained by expression of the plant PAP sequences and proteins of this invention.

BRIEF DESCRIPTION OF THE DRAWINGS

FIG. 2 provides the nucleotide sequence (SEQ ID NO: 3) and deduced amino acid sequence (SEQ ID NO: 12) for the Arabidopsis PAP, ATPAP1.

FIG. 3 provides the nucleotide sequence (SEQ ID NO: 7) and deduced amino acid sequence (SEQ ID NO: 13) for the Arabidopsis PAP, ATPAP2.

FIG. 4 provides the nucleotide sequence (SEQ ID NO: 8) and deduced amino acid sequence (SEQ ID NO: 14) for the Arabidopsis PAP ATPAP3.

FIG. 5 provides the nucleotide sequence of the Brassica napus PAP EST.

FIG. 6 provides the nucleotide sequence (SEQ ID NO: 9) and deduced amino acid sequence (SEQ ID NO: 15) of the corn PAP.

FIG. 7 provides the nucleotide sequence (SEQ ID NO: 10) and deduced amino acid sequence (SEQ ID NO: 16) of the soybean (Glycine sp.) soyPAP1.

FIG. 8 provides the nucleotide sequence (SEQ ID NO: 11) and deduced amino acid sequence (SEQ ID NO: 17) of the soybean (Glycine sp.) soyPAP2.

FIG. 10a, FIG. 10b, FIG. 10c, FIG. 10d, FIG. 10e, FIG. 10f and FIG. 10g provide nucleic acid sequences identified from corn EST libraries searched with ATPAP 1.

FIG. 11 provide s a nucleic acid sequence (SEQ ID NO: 38) identified from Brassica seed EST library which is homologous to the ATPAP3 sequence.

DETAILED DESCRIPTION OF THE INVENTION

Figure 1A:
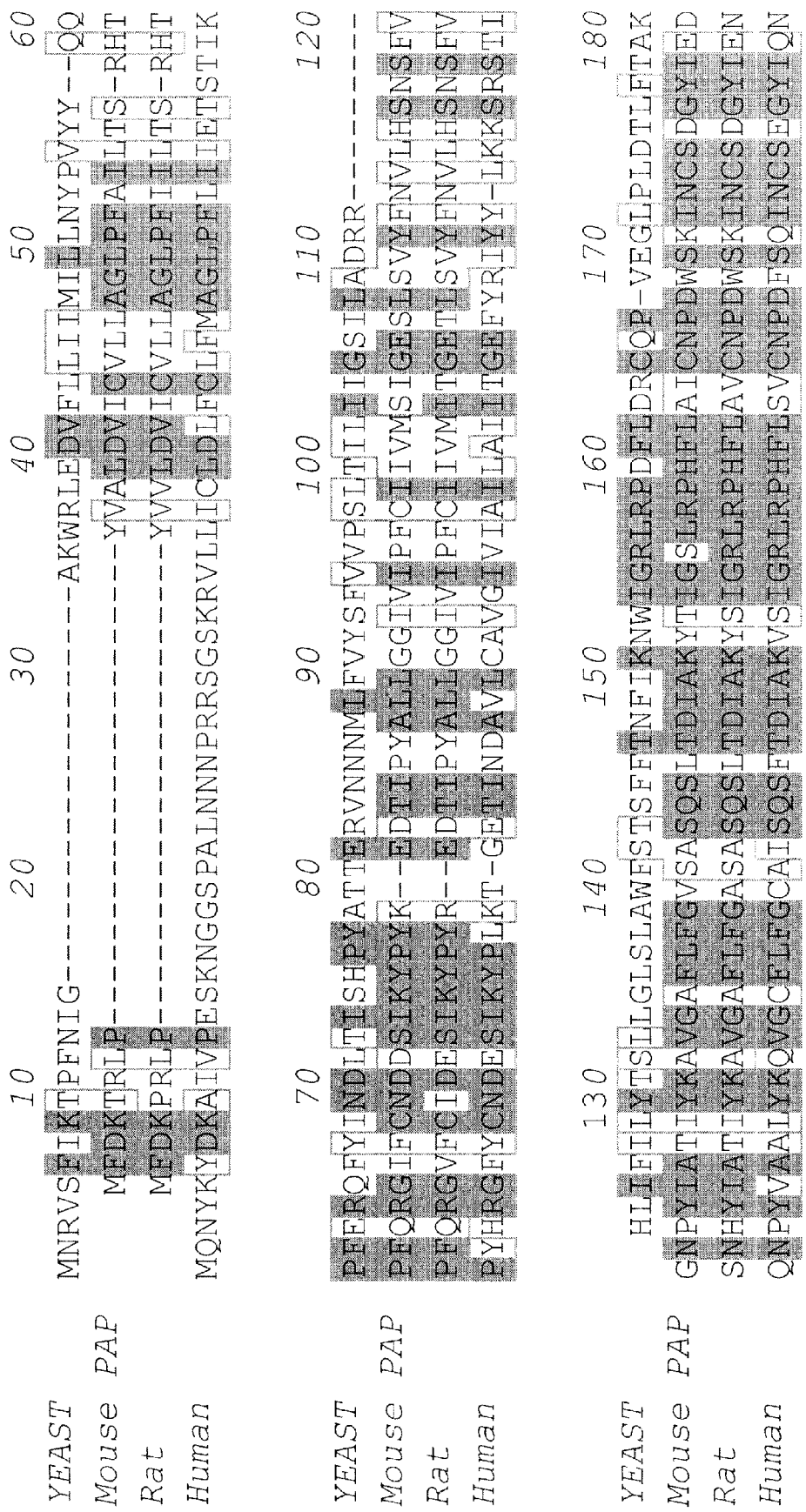
FIG. 1 shows the amino acid sequence alignment of the mouse (SEQ ID NO: 53), rat (SEQ ID NO: 54), human (SEQ ID NO: 55), yeast (SEQ ID NO: 52) and Arabidopsis PAP related sequences. The underlined sequences show the location of the conserved PAP sequences (SEQ ID NOs: 1 and 2) used to search the databases for plant PAP sequences.
Figure 9:
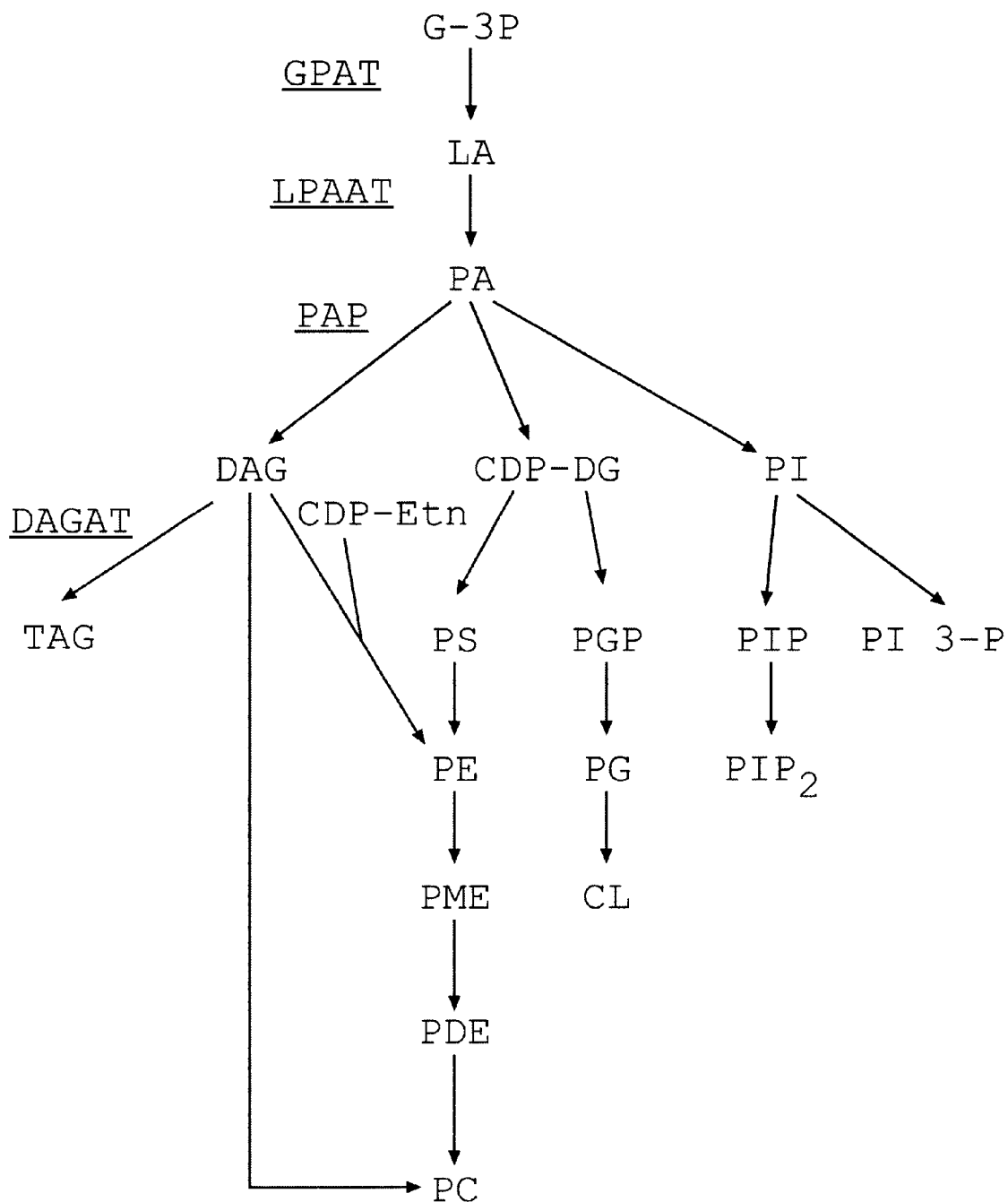
FIG. 9 provides a schematic diagram of the Kennedy pathway for the production of triacylglycerol (TAG) as well as for phosphatidylcholine (PC). G-3P, Glycerol 3 Phosphate; LA, Lysophosphatidic acid; PA, Phosphotidic acid; DAG, Diacylglycerol; TAG, Triacylglycerol; CDP-DG, CDP diacylglycerol; PI Phosphatidylinositol; PS, Phosphatidylserine; PGP, Phosphatidylgycerophosphate; PIP, PI4-phosphate; PI3-P, PI3-phosphate; PE, Phosphatidylethanolamine; PG, Phosphatidylglycerol; $PIP_2$, PI 4,5-bisphosphate; PME, Phosphatidylmonomethylethanolamine; CL, cardiolipin; PDE, Phosphatidyldimethylethanolamine; PC, Phosphatidylcholine, CDP-Etn, CDP Ethanolamine.

In accordance with the subject invention, nucleotide sequences are provided which are capable of coding sequences of amino acids, such as, a protein, polypeptide or peptide, which encode phosphatidic acid phosphatase (also referred to herein as PAP). The novel nucleic acid sequences find use in the preparation of constructs to direct their expression in a host cell. Furthermore, the novel nucleic acid sequences find use in the preparation of plant expression constructs to modify the fatty acid composition as well as the fatty acid content of a host plant cell.

In one embodiment of the present invention, nucleic acid sequences are provided which encode for plant phosphatidic acid phosphatase. An *Arabidopsis thaliana* PAP nucleic acid sequence is identified from databases using oligonucleotide sequences derived from conserved sequences of mouse, rat, human, and yeast phosphatidic acid phosphatase amino acid sequences. The Arabidopsis PAP nucleic acid sequence is used to transform yeast, *E. coli* and plants (Arabidopsis and *Brassica napus*) to confirm the identity of the clone.

In order to identify plant phosphatidic acid phosphatase related nucleic acid and amino acid sequences, a known PAP nucleic acid sequence from a mammalian source was used to identify additional PAP nucleic acid sequences from other mammalian and yeast sources. As described in more detail in the following examples, the nucleic acid and amino acid sequence of a mouse plasmalemma form of PAP is used to identify related DNA and protein sequences from public databases. The protein sequences of the PAP related amino acid sequences are compared using protein alignment software applications known in the art. Two amino acid sequences, TDIAKXXIGRLRPHFLXXC (SEQ ID NO:1) and LSRVSDYKHHWSDV (SEQ ID NO:2), are identified which are highly conserved between the different sequences.

These two peptide sequences are used to search a public EST database to identify Arabidopsis cDNAs which contain the conserved sequences. A cDNA clone is identified from the database as containing the sequence LSRVSDYKHH-WSDV (SEQ ID NO: 2) in two different reading frames.

A full length Arabidopsis PAP nucleic acid sequence is obtained and used to search public and proprietary EST databases. Two additional Arabidopsis PAP related sequences, ATAP2 and ATAP3, as well as PAP related sequences from corn, soybean and Brassica are identified. Sequence alignments between the PAP nucleotide sequences demonstrates a high level of identity between the sequences.

Of particular interest in the present invention, is the use of PAP genes to increase the oil content of seeds. The dephosphorylation of phosphatidic acid by PAP is considered to be the rate limiting step of triacylglycerol biosynthesis in animal tissues (Brindley, (1978), *Int. J. Obes.* 2:7–16). Furthermore, in microsomal preparations from developing cotyledons of safflower and sunflower, the inability to form diacylglycerol from phosphatidic acid in reactions of glycerol phosphate and acyl-CoA suggests that PAP may also be the rate limiting step in plants (Stymne, et al., (1987), *The Biochemistry of Plants*, 9:192–193). Thus, overexpression of a nucleic acid sequence encoding a plant PAP in an oilseed crop may find use in the present invention to increase fatty acid levels in plant tissues.

To confirm the activity and specificity of nucleic acid sequences as PAP enzymes, in vitro assays are performed in *E. coli*, insect and yeast. Expression constructs for *E. coli*, insect and yeast expression are prepared and transformed. Thin Layer Chromatography separation of yeast lipid samples demonstrated the presence of diacylglycerol spots, indicating PAP activity.

All plants utilize PAP proteins in production of TAGs and membrane phospholipids, and thus any given plant species can be considered as a source of additional PAP proteins. Expression of endogenous plant PAP proteins from crop species may find use in the present invention as a method to increase fatty acid compositions in plant tissues. Alternatively, reduced expression of endogenous PAP proteins, for example by using antisense constructs, may find use in the present invention to reduce the levels of membrane lipids in plant tissues.

In another embodiment of the present invention, methods for isolating additional sequences encoding phosphatidic acid phosphatase from other plant species are provided. Such PAP enzymes may find use in producing transgenic plants capable to accumulate high levels of unique oil compositions. For example, identification of a PAP from Cuphea species may have preferential activity for medium-chain phosphatidic acid species. By medium-chain preferring phosphatidic acid species is meant that the enzyme encoded by the PAP nucleic acid sequence demonstrates a preference for dephosphorylating phosphatidic acid species containing C6, C8, C10, C12 and/or C14 fatty acyl groups at the sn-1 and/or sn-2 positions over PA species containing different fatty acyl groups in the sn-1 and/or sn-2 positions.

In addition, identification of a nucleic acid sequence encoding for PAP enzymes from California Bay (*Umbellularia californica*), camphor (*Cinnamomum camphora*), or coconut may also find use in transgenic plants for the increased production of medium-chain fatty acids.

Also of interest in the present invention are PAP enzymes with preferential activity on long chain phosphatidic acid species. Such PAP enzymes may be found in plants such as *Garcinia mangifera* (mangosteen). By long chain preferring phosphatidic acid species is mean that the enzyme encoded by the PAP nucleic acid sequence demonstrates a preference for dephosphorylating phosphatidic acid species containing C16, C18 and/or C18:1 fatty acyl groups at the sn-1 and/or sn-2 positions over PA species containing different fatty acyl groups in the sn-1 and/or sn-2 positions.

Alternatively, PAP enzymes with specific activity on very-long chain phosphatidic acid species may find use in the present invention. Such PAP enzymes may be identified in plants such as Nasturtium species, which accumulates over 90% very long chain fatty acids in its seed oil. By very long-chain phosphatidic acid species is meant that the enzyme encoded by the PAP nucleic acid sequence demonstrates a preference for dephosphorylating phosphatidic acid species containing C20, C22 and longer fatty acyl groups at the sn-1 and/or sn-2 positions over PA species containing different fatty acyl groups in the sn-1 and/or sn-2 positions.

Preferential activity of a plant PAP toward particular chain-length fatty acyl-CoA substrates is determined upon comparison of triacylglycerol product amounts obtained per different chain length acyl-CoA donor substrates. In some cases, the chain length of an acyl group in the sn-1 or sn-2 position may affect the ability of the PAP to dephosphorylate the phosphatidic acid.

Alternatively, PAP enzymes from plants which accumulate long-chain fatty acids (C16 and C18 fatty acids) may discriminate against diacylglycerol species containing short-chain, medium-chain or very long-chain fatty acyl groups in the sn-1 and/or sn-2 positions. Thus, PAP enzymes from plants such as Cuphea species, California Bay, or Nasturtium species may not have preferential activity towards certain diacylglycerol species, but may be less discriminatory towards diacylglycerol species containing short-chain, medium-chain or very long-chain fatty acyl groups.

One skilled in the art will readily recognize that antibody preparations, nucleic acid probes (DNA and RNA) and the like may be prepared and used to screen and recover "homologous" or "related" phosphatidic acid phosphatase from a variety of plant sources. Typically, nucleic acid probes are labeled to allow detection, preferably with radioactivity although enzymes or other methods may also be used. For immunological screening methods, antibody preparations either monoclonal or polyclonal may be utilized. Polyclonal antibodies, although less specific, typically are more useful in gene isolation. For detection, the antibody is labeled using radioactivity or any one of a variety of second antibody/enzyme conjugate systems that are commercially available. Examples of some of the available antibody detection systems are described by Oberfilder (*Focus* (1989) BRL Life Technol., Inc.,11:1–5).

In order to obtain additional PAP sequences, a genomic or other appropriate library prepared from the candidate plant source of interest may be probed with conserved sequences from one or more plant PAP(s) to identify homologously related sequences. Positive clones may be analyzed by restriction enzyme digestion and/or sequencing. When a genomic library is used, one or more sequences may be identified providing both the coding region, as well as the transcriptional regulatory elements of the PAP gene from such plant source. Probes can also be considerably shorter than the entire sequence. Oligonucleotides may be used, for example, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR), especially when highly conserved sequences can be identified. (See, Gould, et al., *PNAS USA* (1989) 86:1934–1938.)

When longer nucleic acid fragments are employed (>100 bp) as probes, especially when using complete or large cDNA sequences, one can still screen with moderately high stringencies (for example using 50% formamide at 37° C. with minimal washing) in order to obtain signal from the target sample with 20–50% deviation, i.e., homologous sequences. (For additional information regarding screening techniques see Beltz, et al., *Meth. Enzymology* (1983) 100:266–285).

Homologous sequences are found when there is an identity of sequence and may be determined upon comparison of sequence information, nucleic acid or amino acid, or through hybridization reactions between a known PAP and a candidate source. Conservative changes, such as Glu/Asp, Val/Ile, Ser/Thr, Arg/Lys and Gln/Asn may also be considered in determining sequence homology. Typically, a lengthy nucleic acid sequence may show as little as 50–60% sequence identity, and more preferably at least about 70% sequence identity, between the target sequence and the given plant PAP of interest excluding any deletions which may be present, and still be considered related. Amino acid sequences are considered homologous by as little as 25% sequence identity between the two complete mature proteins. (See generally, Doolittle, R. F., *OF URFS and ORFS* (University Science Books, CA, 1986.)

In addition, not only can sequences provided herein be used to identify homologous phosphatidic acid phosphatases, but the resulting sequences obtained therefrom may also provide a further method to obtain plant phosphatidic acid phosphatases from other plant sources. In particular, PCR may be a useful technique to obtain related plant PAP from sequence data provided herein. One skilled in the art will be able to design oligonucleotide probes based upon sequence comparisons or regions of typically highly conserved sequence.

Once the nucleic acid sequence is obtained, the transcription, or transcription and translation (expression), of the plant PAP in a host cell is desired to produce a ready source of the enzyme and/or modify the composition of fatty acids and/or triglycerides found therein. Other useful applications may be found when the host cell is a plant host cell, in vitro and in vivo.

Nucleic acids (genomic DNA, plasmid DNA, cDNA, synthetic DNA, mRNA, etc.) encoding phosphatidic acid phosphatase or amino acid sequences of the purified enzymes, which permit design of nucleic acid probes facilitating the isolation of DNA coding sequences therefor, are known in the art and are available for use in the methods of the present invention. It is generally recognized to an artisan skilled in the field to which the present invention pertains that the nucleic acid sequences provided herein and the amino acid sequences derived therefrom may be used to isolate other potential PAP genes from GenBank using DNA and peptide search techniques generally known in the art.

In addition to the sequences described in the present invention, DNA coding sequences useful in the present invention can be derived from algae, fungi, bacteria, mammalian sources, plants, etc. Homology searches in existing databases using signature sequences corresponding to conserved nucleotide and amino acid sequences of PAP can be employed to isolate equivalent, related genes from other sources such as plants and microorganisms. Searches in EST databases can also be employed. Furthermore, the use of DNA sequences encoding enzymes functionally enzymatically equivalent to those disclosed herein, wherein such DNA sequences are degenerate equivalents of the nucleic acid sequences disclosed herein in accordance with the degeneracy of the genetic code, is also encompassed by the present invention. Demonstration of the functionality of coding sequences identified by any of these methods can be carried out by complementation of mutants of appropriate organisms, such as Synechocystis, Shewanella, yeast, Pseudomonas, Rhodobacteria, etc., that lack specific biochemical reactions, or that have been mutated. The sequences of the DNA coding regions can be optimized by gene resynthesis, based on codon usage, for maximum expression in particular hosts.

The nucleic acid sequences which encode plant phosphatidic acid phosphatases may be used in various constructs, for example, as probes to obtain further sequences. Alternatively, these sequences may be used in conjunction with appropriate regulatory sequences to increase levels of the respective PAP of interest in a host cell for recovery or study of the enzyme in vitro or in vivo or to decrease levels of the respective PAP of interest for some applications when the host cell is a plant entity, including plant cells, plant parts (including but not limited to seeds, cuttings or tissues) and plants.

Thus, depending upon the intended use, the constructs may contain the nucleic acid sequence which encodes the entire PAP protein, or a portion thereof. For example, where antisense inhibition of a given PAP protein is desired, the entire PAP sequence is not required. Furthermore, where PAP constructs are intended for use as probes, it may be advantageous to prepare constructs containing only a particular portion of a PAP encoding sequence, for example a sequence which is discovered to encode a highly conserved PAP region.

As discussed above, nucleic acid sequence encoding a plant or other PAP of this invention may include genomic, cDNA or MRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

A cDNA sequence may or may not contain pre-processing sequences, such as transit peptide sequences or targeting sequences to facilitate delivery of the PAP protein (such as mitochondrial PAP) to a given organelle or membrane location. The use of any such precursor PAP DNA sequences is preferred for uses in plant cell expression. A genomic PAP sequence may contain the transcription and translation initiation regions, introns, and/or transcript termination regions of the plant PAP, which sequences may be used in a variety of DNA constructs, with or without the PAP structural gene. Thus, nucleic acid sequences corresponding to the plant PAP of this invention may also provide signal sequences useful to direct protein delivery into a particular organellar or membrane location, 5' upstream non-coding regulatory regions (promoters) having useful tissue and timing profiles, 3' downstream non-coding regulatory regions useful as transcriptional and translational regulatory regions, and may lend insight into other features of the gene.

Once the desired plant or other PAP nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant or other PAP of this invention may be combined with other non-native, or "heterologous", sequences in a variety of ways. By "heterologous" sequences is meant any sequence which is not naturally found joined to the native (or wild-type) PAP, including, for example, combinations of nucleic acid sequences from the same plant which are not naturally found joined together.

The DNA sequence encoding a plant or other PAP of this invention may be employed in conjunction with all or part of the gene sequences normally associated with the PAP. In its component parts, a DNA sequence encoding PAP is combined in a DNA construct having, in the 5' to 3' direction of transcription, a transcription initiation control region capable of promoting transcription and translation in a host cell, the DNA sequence encoding plant PAP and a transcription and translation termination region.

Potential host cells include both prokaryotic and eukaryotic cells. A host cell may be unicellular or found in a multicellar differentiated or undifferentiated organism depending upon the intended use. Cells of this invention may be distinguished by having a PAP foreign to the wild-type cell present therein, for example, by having a recombinant nucleic acid construct encoding a plant PAP therein not native to the host species.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae,* including genes such as beta-galactosidase, T7 polymerase, tryptophan E and the like.

In a preferred embodiment, the constructs will involve regulatory regions functional in plants which provide for modified production of plant PAP, and, possibly, modification of the fatty acid composition. The open reading frame coding for the plant PAP or functional fragment thereof will be joined at its 5' end to a transcription initiation regulatory region. In embodiments wherein the expression of the PAP protein is desired in a plant host, the use of all or part of the complete plant PAP gene is desired; namely all or part of the 5' upstream non-coding regions (promoter) together with the structural gene sequence and 3' downstream non-coding regions may be employed.

If a different promoter is desired, such as a promoter native to the plant host of interest or a modified promoter, i.e., having transcription initiation regions derived from one gene source and translation initiation regions derived from a different gene source, numerous transcription initiation regions are available which provide for a wide variety of constitutive or regulatable, e.g., inducible, transcription of the structural gene functions. The transcription/translation initiation regions corresponding to such structural genes are found immediately 5' upstream to the respective start codons. Among transcriptional initiation regions used for plants are such regions associated with the T-DNA structural genes such as for nopaline and mannopine synthases, the 19S and 35S promoters from CaMV, and the 5' upstream regions from other plant genes such as napin, ACP, SSU, PG, zein, phaseolin E, and the like. Enhanced promoters, such as double 35S, are also available for expression of PAP sequences. For such applications when 5' upstream noncoding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of issued U.S. Pat. Nos. 5,608,152 and 5,530,194, which references are hereby incorporated by reference. Transcription initiation regions which are preferentially expressed in seed tissue, i.e., which are undetectable in other plant parts, are considered desirable for TAG modifications in order to minimize any disruptive or adverse effects of the gene product.

Regulatory transcript termination regions may be provided in DNA constructs of this invention as well. Transcript termination regions may be provided by the DNA sequence encoding the plant PAP or a convenient transcription termination region derived from a different gene source, for example, the transcript termination region which is naturally associated with the transcript initiation region. Where the transcript termination region is from a different gene source, it will contain at least about 0.25 kb, preferably about 1–3 kb of sequence 3' to the structural gene from which the termination region is derived.

Plant expression or transcription constructs having a plant PAP as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledenous and monocotyledenous species alike and will be readily applicable to new and/or improved transformation and regulation techniques.

Likewise, the expression of any PAP which is capable of preferentially dephosphorylating a phosphatidic acid containing a medium-chain fatty acyl group in the sn-2 position is also desired for applications in crop species engineered to contain medium-chain fatty acids.

Further plant genetic engineering applications for PAP proteins of this invention include their use in preparation of structured plant lipids which contain TAG molecules having desirable fatty acyl groups incorporated into particular positions on the TAG molecules. For example, in Brassica plants, the sn-2 position of TAG contains mainly unsaturated fatty acyl groups. In certain applications, it may be desirable to have saturated fatty acids at the sn-2 position, and thus a PAP from a different plant source may be identified as having preferential activity on specific phosphatidic acid substrates, for example 16:0 or 18:0 in the sn-2 position, and used for transformation of Brassica.

In addition, in Brassica plants which contain high levels of erucic acid (22:1) in their seed oils (high erucic acid rapeseed or HEAR), little or no 22:1 is found in the sn-2 position of the TAG molecules. A "tri-erucic" HEAR plant having 22:1 in all three of the TAG sn positions is desirable. Such a seed oil may be obtained by expression of a PAP which is preferentially active on phosphatidic acid species containing 22:1 in the sn-2 position in HEAR plants. A gene encoding such an PAP may be identified from meadowfoam (Limnanthes alba), whose seeds accumulate oil containing erucic acid (22:1) in all three sn positions.

In order to increase TAG biosynthesis, and thereby increasing fatty acids, in a plant tissue, coexpression of a plant or other PAP in a plant tissue with a second gene involved in fatty acid biosynthesis may also find use in the present invention. For example, coexpression of a PAP sequence in plant seed tissue with a DNA sequence encoding for another protein involved in TAG biosynthesis, such as LPAAT (U.S. patent application Ser. No. 07/458,109, the entirety of which is incorporated herein by reference) may increase the flux through the kennedy pathway and increase the total fatty acids produced in the seed tissue. Furthermore, other genes involved in TAG biosynthesis, for example DAGAT may be coexpressed with a PAP encoding sequence of the present invention to increase oil levels in plant tissue.

In addition, coexpression of a PAP sequence of the present invention with a sequence encoding an enzyme involved in fatty acid biosynthesis may also find use in the production of increased levels of plant oils. In particular, coexpression of a PAP sequence with a sequence encoding a medium-chain thioesterase may allow for the increased production of medium-chain fatty acids in a plant oil. Such medium-chain thioesterases are known in the art. Examples of medium-chain thioesterases are described in U.S. Pat. Nos. 5,455,167 and 5,667,997, the entireties of which are incorporated herein by reference.

Any means for producing a plant comprising a PAP gene or both a PAP gene and second oil biosynthesis gene are encompassed by the present invention. For example, the second oil biosynthesis gene of interest can be used to transform a plant at the same time as the PAP encoding sequence either by inclusion of both expression constructs in a single transformation vector or by using separate vectors, each of which express desired genes. The second oil biosynthesis gene can be introduced into a plant which has already been transformed to express a PAP encoding sequence, or alternatively, transformed plants, one expressing a PAP encoding sequence and one expressing a second oil biosynthesis gene, can be crossed to bring the genes together in the same plant.

As mentioned above, phosphatidic acid phosphatase also catalyzes the first commited step in the biosynthesis of important membrane phospholipids phosphatidylethanolamine (PE) and phosphatidylcholine (PC) via the CDP-ethanolamine (CDP-Etn)and CDP-choline-based kennedy pathway (Kennedy, et al. (1956) *J. Biol. Chem.* 222:193–214).

In addition, in mammalian cells, PAP is thought to be involved with cellular signal transduction to control the balance between diacylglycerol and phosphatidic acid, which are both secondary messengers. Thus, constructs to direct the expression of the PAP sequences of the present invention in a plant host cell may find use in altering cellular signal transduction events involving DAG and PA as well as DAG and PA products.

Furthermore, the PAP sequences of the present invention may find use in expression constructs to generate transgenic plants with altered membrane lipids or phospholipid levels in the host plant. As phospholipids are involved in cell signaling, altered phospholipid levels may produce plants which have an altered cellular metabolism.

Furthermore, for increased production of a particular chain length fatty acid, for example medium-chain fatty acids, coexpression of a plant or other PAP in a plant tissue with a second DNA sequence encoding for enzymes involved in the production of medium-chain, or other chain length, fatty acids may find use in the present invention. DNA sequences encoding for thioesterases (for example U.S. Pat. Nos. 5,298,421, 5,667,997 the entirety of which are incorporated herein by reference) or fatty acid synthases (U.S. patent application Ser. No. 08/827,828 the entirety of which is incorporated herein by reference) are examples of enzymes involved in the production of various chain length fatty acids.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to Agrobacterium infection may be successfully transformed via tripartite or binary vector methods of Agrobacterium mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming host plant cells, the expression or transcription construct bordered by the T-DNA border region (s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli,* and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Included with the expression construct and the T-DNA will be one or more markers, which allow for selection of transformed Agrobacterium and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The invention now being generally described, it will be more readily understood by reference to the following examples which are included for purposes of illustration only and are not intended to limit the present invention.

EXAMPLES

Example 1

Identification of PAP Sequences

The gene encoding a mouse plasmalemma form of phosphatidic acid phosphatase has been previously cloned and sequenced (Kai, et al. (1996), *J. Biol. Chem.,* 271:18931–18938). The protein sequence w as obtained from Genbank and used to search p rotei n and DNA databases to identify related sequences. Sequences from rat, human, C. elegans and yeast were identified as being related to the mouse PAP sequence. The sequences of PAP from mouse, rat, human and yeast were aligned (FIG. 1) using MacVector (Oxford Molecular, Inc.), and two conserved peptide sequences were identified; TDIAKXXIGRLR-PHFLXXC (SEQ ID NO:1) and LSRVSDYKHHWSDV (SEQ ID NO: 2). These two protein sequences were used to search the Arabidopsis EST database, and one cDNA clone, 158J20XP, was identified as containing an amino acid sequence motif 71% similar to the LSRVSDYKHHWSDV motif (SEQ ID NO: 2).

The cDNA clone of 158J20XP (also referred to as ATPAP1) was obtained from the Arabidopsis Biological Resource Center (Columbus, Ohio). Full length DNA sequence was determined using an ABI automated sequencer and is shown in FIG. 2 (SEQ ID NO:3). Analysis of the DNA sequence using MacVector indicated an 870 base open reading frame that contained the LSRVSDYKH-HWSDV (SEQ ID NO: 2) PAP-related motif.

The cDNA sequence of PAP of was amplified from ATPAP1 using the Polymerase Chain Reaction (PCR) and cloned into a vector for further manipulations. The cDNA was amplified using the following primers: 5' CCA-GATCTGC<u>ATG</u>CTCAACGTACGCTCTCTAGCTC 3' (SEQ ID NO:4) and 5' CCAGATCTCTCGAGACAATGC-CTGAAATTCATTTGGGT 3' (SEQ ID NO:5) using the reaction conditions of 25 cycles of the following: 94° C. for 15 seconds, 47° C. for 30 seconds, 72° C. for 2 minutes using pfu polymerase (Stratagene, La Jolla, Calif.) following the manufacturers instructions.

The nucleotide sequences of the primers were designed according to the sequence obtained from the Arabidopsis EST clone ATAP1. The forward primer containing PAP gene encoding sequence from the 5' end of the cDNA, including the ATG start codon (underlined above) and restriction cloning sites. The reverse primer contains complementary sequence to sequences in the 3' untranslated region and restriction cloning sites.

Following PCR using the Forward and Reverse primers and RNA prepared as described above , the resulting fragment was cloned into digested EcoRV digested pZERO2 (Invitrogen, Carlsbad, Calif.) to create the plasmid pCGN8521. The nucleotide sequence of the cloned Arabidopsis PAP cDNA was determined to insure that no errors had been introduced in the PCR process.

1B. Identification of Plant PAP Related Sequences

The sequence from ATPAP1 was used to search the EST database, and a Brassica EST was identified (FIG. 5, Genbank accession H74464, clone RRM1112 SEQ ID NO:6). The identified Brassica EST was aligned with the DNA sequence from ATPAP1 using MacVector. Alignment of these two sequences demonstrates that over the 257 nucleotides aligned between the Brassica and Arabidopsis sequences, 172 nucleotides were identical (67% identity).

The Arabidopsis PAP sequence was also used to search proprietary databases containing corn, soybean and Arabidopsis EST sequences. Two additional Arabidopsis PAP sequences were identified, ATPAP2 (FIG. 3; SEQ ID NO:7) and ATPAP3 (FIG. 4; SEQ ID NO:8). Several corn ESTs and two soybean ESTs were identified, and the largest clone was obtained for further cloning and analysis. The DNA sequence of the Arabidopsis PAP corn and soybean ESTs were determined and a full length sequences were obtained using RACE-PCR, and the sequence obtained for the corn PAP sequence is shown in FIG. 6 (SEQ ID: 9) and the two soybean PAP sequences are shown in FIGS. 7 and 8 (SEQ ID NO:10 and SEQ ID NO:11). In addition, EST sequences similar to the ATPAP1 sequence are identified from corn EST databases. The results of the search are provided in FIG. 10a, FIG. 10b, FIG. 10c, FIG. 10d, FIG. 10e, FIG. 10f and FIG. 10g. Furthermore, a sequence was identified with the ATPAP3 sequence from a Brassica seed EST library (FIG. 11).

Example 2
Yeast Expression of an Arabidopsis PAP

Constructs were prepared to express the PAP protein in yeast. The vector pCGN8521 was digested with BglII and SphI, and the PAP encoding fragment was cloned into the yeast expression vector pYES2 (Invitrogen, Carlsbad, Calif.), digested with BamHI and SphI, to yield plasmid pCGN8523.

Plasmids pCGN8523 and pYES2 were transformed into yeast strain InvSC1 (Invitrogen) using a standard lithium acetate procedure (Ausubel et al. *Current Protocols in Molecular Biology* pp13.0.1–13.13.9 (1997)). Standard yeast manipulations and media are described in Ausubel et al. (Ausubel et al. *Current Protocols in Molecular Biology* pp13.0.1–13.13.9 (1997)), and summarized here. Fifty milliliter cultures of the recombinant yeast were grown to stationary phase in SC (lacking uracil) medium with glucose. Twenty OD 600 units of cells were centrifuged and washed with SC (lacking uracil) medium with no sugar. The cells were subsequently resuspended in 100 ml of SC (lacking uracil) medium with galactose. This galactose induces expression of genes cloned under control of the gal promoter in pYES2. The yeast were grown for 2 days. Fifty milliliters of yeast cells were pelleted by centrifugation, and the lipids were extracted in 5 ml of chloroform: methanol:0.025 MHCl (5:10:4). Phase separation was accomplished by adding 1.2 ml of Chloroform and 1.2 ml of water. The lower chloroform phase was removed and dried under a stream of nitrogen gas. The lipid samples were resuspended in 50 ul of Hexane and loaded on a Silica TLC plate. The TLC plate was developed in Hexane:Diethyl ether:Acetic Acid (50:50:2), and the lipids were visualized by iodine staining. Two of the three lipid samples from yeast transformed with pCGN8523 showed visible diacylglycerol spots, while none of the 4 samples extracted from untransformed yeast or yeast transformed with pYES2 showed diacylglycerol spots. These data confirm that the clone Arabidopsis cDNA encodes PAP.

Example 3
Baculovirus Expression of Arabidopsis PAP

Constructs are prepared to direct expression of the ATPAP1, ATPAP2 and ATPAP3 sequences in cultured insect cells. The entire coding region of ATPAP2 is amplified from the EST clone LIB24-018-Q1-E1-A8 using oligonucleotide primers 5'-GGATCCGCGGCCGCAGAAATGCAGGAGATAGA TCTTAG-3' (SEQ ID NO: 39) and 5'-CCTGCAGGAAGCTTTCATCTGGGAGCGGTGGAAG-3' (SEQ ID NO: 40) in a polymerase chain reaction (PCR). The PCR product was subcloned into pCR2.1 lTopo (Invitrogen). Double stranded DNA sequence was obtained to verify that no errors were introduced by the PCR amplification. The resulting plasmid was designated pCGN8645.

The entire coding region of ATPAP3 is amplified from the EST clone LIB25-028-Q1-E1-E11 using oligonucleotide primers 5'-GAGCTCCTGCAGGAAGCTTTCAGCCTCTACCAG TTTCTACATCC-3' (SEQ ID NO: 41) and 5'-GGATCCGCGGCCGCACAGGATGAGAGAGGCAC AGCTAGG-3' (SEQ ID NO: 42) in a polymerase chain reaction (PCR). The PCR product was subcloned into pCR2.1 Topo (Invitrogen). Double stranded DNA sequence was obtained to verify that no errors were introduced by the PCR amplification. The resulting plasmid was designated pCGN8646.

The construct pCGN8521 was digested with BamHI and EcoRi and a fragment containing the ATPAP1 coding region was purified by gel electrophoresis. The fragment containing the entire coding region of ATPAP1 was subcloned into the baculovirus expression vector pFastBacl (Gibco-BRL, Gaithersburg, Md.) that had been digested with BamHI and EcoRI. The resulting plasmid was designated pCGN8662. DNA sequence analysis confirmed the integrity of the cloning junctions.

The construct pCGN8645 was digested with NotI and Sse8387I and a fragment containing the ATPAP2 coding region was purified by gel electrophoresis. The fragment containing the entire coding region of ATPAP2 was subcloned into the baculovirus expression vector pFastBac 1 (Gibco-BRL, Gaithersburg, Md.) that had been digested with NotI and PstI. The resulting plasmid was designated pCGN8663. DNA sequence analysis confirmed the integrity of the cloning junctions.

The construct pCGN8646 was digested with NotI and Sse8387I and a fragment containing the ATPAP3 coding region was purified by gel electrophoresis. The fragment containing the entire coding region of ATPAP3 was subcloned into the baculovirus expression vector pFastBac 1 (Gibco-BRL, Gaithersburg, Md.) that had been digested with NotI and PstI. The resulting plasmid was designated pCGN8664. DNA sequence analysis confirmed the integrity of the cloning junctions.

The baculovirus expression constructs pCGN8662, pCGN8663 and pCGN8664 are transformed and expressed using the BAC-to-BAC Baculovirus Expression System (Gibco-BRL, Gaithersburg, Md.) according to the manufacturers directions, except harvesting of recombinant viruses was done 5 days post-transfection. The supernatant from the transfection mixture is used for generating virus stock which in turn is used for infecting Sf9 cells for use in the assay.

The transformed insect cells can be assayed for phosphatidic acid phosphatase activity using methods described herein.

Example 4
Plant Expression of Arabidopsis PAP

Vectors for the expression of PAP in plants were constructed in both sense and antisense orientations. Constructs were prepared for constitutive and seed specific expression of PAP.

A plasmid containing the napin cassette derived from pCGN3223 (described in U.S. Pat. No. 5,639,790, the entirety of which is incorporated herein by reference) was modified to make it more useful for cloning large DNA fragments containing multiple restriction sites, and to allow the cloning of multiple napin fusion genes into plant binary transformation vectors. An adaptor comprised of the self annealed oligonucleotide of sequence CGCGATTTAAATG-GCGCGCCCTGCAGGCGGCCGCCTG-CAGGGCGCGCCATTTAA AT (SEQ ID NO. 43) was ligated into the cloning vector pBC SK+(Stratagene) after digestion with the restriction endonuclease BssHII to construct vector pCGN7765. Plamids pCGN3223 and pCGN7765 were digested with NotI and ligated together. The resultant vector, pCGN7770, contains the pCGN7765 backbone with the napin seed specific expression cassette from pCGN3223.

The cloning cassette, pCGN7787, essentially the same regulatory elements as pCGN7770, with the exception of the napin regulatory regions of pCGN7770 have been replaced with the double CAMV 35S promoter and the tml polyadenylation and transcriptional termination region.

A binary vector for plant transformation, pCGN5139, was constructed from pCGN1558 (McBride and Summerfelt, (1990) Plant Molecular Biology, 14:269–276). The polylinker of pCGN1558 was replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139.

A series of turbo binary vectors are constructed to allow for the rapid cloning of DNA sequences into binary vectors containing transcriptional initiation regions (promoters) and transcriptional termination regions.

The plasmid pCGN8618 was constructed by ligating oligonucleotides 5'-TCQAGGATCCGCGGCCGCAAGCTTCCTGCAGG-3' (SEQ ID NO. 44) and 5'-TCGACCTGCAGGAAGCTTGCGGCCGCGGATCC-3' (SEQ ID NO. 45) into SalI/XhoI-digested pCGN7770. A fragment containing the napin promoter, polylinker and napin 3' region was excised from pCGN8618 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8622.

The plasmid pCGN8619 was constructed by ligating oligonucleotides 5'-TCGACCTGCAGGAAGCTTGCGGCCGCGGATCC-3' (SEQ ID NO. 45) and 5'-TCGAGGATCCGCGGCCGCAAGCTTCCTGCAGG-3' (SEQ ID NO. 44) into SalI/XhoI-digested pCGN7770. A fragment containing the napin promoter, polylinker and napin 3' region was removed from pCGN8619 by digestion with Asp718 I; the fragment was blunt-ended by filling in the 5' overhangs with Klenow fragment then ligated into pCGN5139 that had been digested with Asp718 I and HindIII and blunt-ended by filling in the 5' overhangs with Klenow fragment. A plasmid containing the insert oriented so that the napin promoter was closest to the blunted Asp7281 site of pCGN5139 and the napin 3' was closest to the blunted HindIII site was subjected to sequence analysis to confirm both the insert orientation and the integrity of cloning junctions. The resulting plasmid was designated pCGN8623.

The plasmid pCGN8620 was constructed by ligating oligonucleotides 5'-TCGAGGATCCGCGGCCGCAAGCTTCCTGCAGG AGCT-3' (SEQ ID NO. 46) and 5'-CCTGCAGGAAGCTTGCGGCCGCGGATCC-3' (SEQ ID NO. 47) into SalI/SacI-digested pCGN7787. A fragment containing the d35S promoter, polylinker and tml 3' region was removed from pCGN8620 by complete digestion with Asp718 I and partial digestion with NotI. The fragment was blunt-ended by filling in the 5' overhangs with Klenow fragment then ligated into pCGN5139 that had been digested with Asp718 I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8624.

The plasmid pCGN8621 was constructed by ligating oligonucleotides 5'-TCGACCTGCAGGAAGCTTGCGGCCGCGGATCC AGCT-3' (SEQ ID NO. 48) and 5'-GGATCCGCGGCCGCAAGCTTCCTGCAGG-3' (SEQ ID NO. 49) into SalI/SacI-digested pCGN7787. A fragment containing the d35S promoter, polylinker and tml 3' region was removed from pCGN8621 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8625.

The plasmid construct pCGN8640 is a modification of pCGN8624 described above. A 938bp PstI fragment isolated from transposon Tn7 which encodes bacterial spectinomycin and streptomycin resistance (Fling et al. (1985), Nucleic Acids Research 13(19):7095–7106), a determinant for *E. coli* and Agrobacterium selection, was blunt ended with Pfu polymerase. The blunt ended fragment was ligated into pCGN8624 that had been digested with SpeI and blunt ended with Pfu polymerase. The region containing the PstI fragment was sequenced to confirm both the insert orientation and the integrity of cloning junctions.

The spectinomycin resistance marker was introduced into pCGN8622 and pCGN8623 as follows. A 7.7 Kbp AvrII-SnaBI fragment from pCGN8640 was ligated to a 10.9 Kbp AvrII-SnaBI fragment from pCGN8623 or pCGN8622, described above. The resulting plasmids were pCGN8641 and pCGN8643, respectively.

The plasmid pCGN8644 was constructed by ligating oligonucleotides 5'-GATCACCTGCAGGAAGCTTGCGGCCGCGGATCC AATGCA-3' (SEQ ID NO. 50) and 5'-TTGGATCCGCGGCCGCAAGCTTCCTGCAGGT-3' (SEQ ID NO. 51) into BamHI-PstI digested pCGN8640.

Plasmid pCGN8521 was digested with BglII and the fragment encoding PAP was cloned in the napin cassette of pCGN7770 after digestion with BglII. The resultant plasmids are pCGN8607 which contains the PAP gene in the sense orientation and pCGN8608 which contains the PAP gene in the antisense orientation. The two plasmids were digested with Asp718 and the napin/PAP gene fusions were cloned into the Asp718 digested binary vector pCGN5139. Plasmid pCGN8611 contains the napin/sense PAP gene from pCGN8607, and plasmid pCGN8612 contains the napin/antisense PAP gene from pCGN8608.

Plasmid pCGN8521 was digested with BglII and the fragment encoding PAP was cloned in the CAMV35S cassette of pCGN7787 after digestion with BamHI. The resultant plasmids were pCGN8609 which contains the PAP gene in the sense orientation and pCGN8610 which contains the PAP gene in the antisense orientation. The two plasmids were digested with Asp718 and the CAMV35S/PAP gene fusions were cloned into the Asp718 digested binary vector pCGN5139. Plasmid pCGN8613 contains the CAMV35S/sense PAP gene from pCGN8609, and plasmid pCGN8614 contains the CAMV35S/antisense PAP gene from pCGN8610.

A fragment containing the ATPAP2 coding region was removed from pCGN8645 by digestion with NotI and Sse8387I. The fragment was ligated into PstI-NotI digested pCGN8643. The resulting plasmid was designated pCGN8647. DNA sequence analysis confirmed the integrity of the cloning junctions.

A fragment containing the ATPAP2 coding region was removed from pCGN8645 by digestion with NotI and Sse8387 I. The fragment was ligated into PstI-NotI digested pCGN8641. The resulting plasmid was designated pCGN8648. DNA sequence analysis confirmed the integrity of the cloning junctions.

A fragment containing the ATPAP2 coding region was removed from pCGN8645 by digestion with NotI and Sse8387I. The fragment was ligated into PstI-NotI digested pCGN8640. The resulting plasmid was designated pCGN8649. DNA sequence analysis confirmed the integrity of the cloning junctions.

A fragment containing the ATPAP2 coding region was removed from pCGN8645 by digestion with NotI and Sse8387 I. The fragment was ligated into PstI-NotI digested pCGN8644. The resulting plasmid was designated pCGN8650. DNA sequence analysis confirmed the integrity of the cloning junctions.

A fragment containing the ATPAP3 coding region was removed from pCGN8646 by digestion with NotI and Sse8387 I. The fragment was ligated into PstI-NotI digested pCGN8643. The resulting plasmid was designated pCGN8651. DNA sequence analysis confirmed the integrity of the cloning junctions.

A fragment containing the ATPAP3 coding region was removed from pCGN8646 by digestion with NotI and Sse8387 I. The fragment was ligated into PstI-NotI digested pCGN8641. The resulting plasmid was designated pCGN8652. DNA sequence analysis confirmed the integrity of the cloning junctions.

A fragment containing the ATPAP3 coding region was removed from pCGN8646 by digestion with NotI and Sse8387 I. The fragment was ligated into PstI-NotI digested pCGN8640. The resulting plasmid was designated pCGN8653. DNA sequence analysis confirmed the integrity of the cloning junctions.

A fragment containing the ATPAP3 coding region was removed from pCGN8646 by digestion with NotI and Sse8387 I. The fragment was ligated into PstI-NotI digested pCGN8644. The resulting plasmid was designated pCGN8654. DNA sequence analysis confirmed the integrity of the cloning junctions.

Example 5

Plant Transformation

A variety of methods have been developed to insert a DNA sequence of interest into the genome of a plant host to obtain the transcription or transcription and translation of the sequence to effect phenotypic changes.

Transgenic Brassica plants are obtained by Agrobacterium-mediated transformation as described by Radke et al. (*Theor. Appl. Genet.* (1988) 75:685–694; *Plant Cell Reports* (1992) 11:499–505). Transgenic *Arabidopsis thaliana* plants may be obtained by Agrobacterium-mediated transformation as described by Valverkens et al., (*Proc. Nat. Acad. Sci.* (1988) 85:5536–5540), or as described by Bent et al. ((1994), Science 265:1856–1860), or Bechtold et al. ((1993), C.R.Acad.Sci, Life Sciences 316:1194–1199) or Clough, et al. (1998) Plant J., 16:735–43. Other plant species may be similarly transformed using related techniques.

Alternatively, microprojectile bombardment methods, such as described by Klein et al. (*Bio/Technology* 10:286–291) may also be used to obtain nuclear transformed plants.

Example 6

Transgenic Plant Analysis

Transgenic plants expressing phosphatidic acid phosphatase are analyzed using techniques known in the art. Enzyme assays are used to determine the PAP activity in leaves of control plants, plants transformed with pCGN8613, and plants transformed with pCGN8614. Leaf lipids are analyzed by thin layer chromatography to determine glycerolipid composition of the leaf lipids. Seed lipids of the control plants, plants transformed with pCGN8611, and plants transformed with pCGN8612 are analyzed for alterations in the levels of diacylglycerol, triacylglycerol, or phospholipids.

The fatty acid compositions of different lipid classes extracted from mature seeds can be examined by the following method. Analyses of the acyl compositions of the sn-2 and sn-1+3 positions of TAG are conducted using the pancreatic lipase protocol (3rockerhoff (1975), supra). Ideally with this protocol, the lipase cleaves fatty acids from the sn-1 and sn-3 positions, and not from the sn-2 position. Thus, the fatty acids in the resulting mono-glyceride are presumed to be those in the sn-2 position. However, it is noted that those previously attempting to study TAG having shorter-chain fatty acids by this method (Entressangles et al. (1964) *Biochim. Biophys. Acta* 84:140–148), reported that shorter-chain fatty acids located at the sn-2 position were quickly hydrolyzed during such a digestion, which the authors reported to be the result of a spontaneous migration of internal shorter-chain fatty acids towards outer positions in diglycerides and monoglycerides.

Oil distilled from mature seeds may be subjected to a pancreatic lipase digestion protocol modified from Brockerhoff et al., supra, to minimize acyl migration. This distinguishes acyl compositions of the sn-2 and sn-1+3 combined positions. The modifications are as follows: pH is lowered to neutrality, reaction time is shortened from 15 to 3 minutes, samples are maintained at acidic pH thereafter, and digestion products are chromatographed on borate-impregnated TLC plants. The chromatographed products are then eluted and analyzed as fatty acid methyl esters as before.

PAP enzyme activity is analyzed using a modified method described by Lin and Carrnan ((1989), *J. Biol. Chem.*, 264, 8641–8645). The modifications involve the use of $^{14}$C[U]-glycerol dipalmitoyl-PA and monitoring the production of $^{14}$C-dipalmitoyl DAG.

In a 100 ul assay volume containing 20 ul sample, the following assay components are added: 500 uM $^{14}$C-PA (71.64 Ci/mole), 2 mM $MgCl_2$, 10 mM beta-mercaptoethanol, 50 mM NaCl and 0.3% Triton X-100 in 50 mM HEPES pH 7.5. Assays are allowed to run for 30 minutes at 30° C. then stopped with 1.5 mls heptane:isopropanol: 0.5M sulfuric acid (20:80:2). Products are extracted by adding 0.1 ml 1M sodium bicarbonate and 1 ml heptane. The organic phase was transferred to a new vial and washed with 1 ml 1M NaCl. A portion of the organic phase was counted by a liquid scintillation counter and the remaining sample was evaporated under nitrogen gas, resuspended in heptane, and spotted on a silica gel-G thin layer chromatographic plate. The TLC plate was migrated in hexane:diethyl ether: acetic acid (70:30:2) then scanned with a radio-image analyzer. The radioactivity incorporated into DAG was quantitated.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. An isolated DNA sequence encoding a plant phosphatidic acid phosphatase protein, wherein said plant phosphatidic acid phosphatase protein encoded by said nucleic acid molecule includes an amino acid fragment having at least 70% sequence identity to SEQ ID NO: 2.

2. The DNA sequence of claim 1, wherein said phosphatidic acid phosphatase protein is found in soybean.

3. The DNA sequence of claim 2, wherein said phosphatidic acid phosphatase protein comprises an amino acid sequence of SEQ ID NO: 16.

4. The DNA sequence of claim 2, wherein said phosphatidic acid phosphatase protein comprises an amino acid sequence of SEQ ID NO: 17.

5. A recombinant DNA construct comprising a DNA sequence of any one of claims 1 and 2–4.

6. A recombinant DNA construct comprising, as operably linked in the 5' to 3' direction of transcription, a transcriptional initiation region functional in a plant cell, a DNA structural gene sequence encoding a plant phosphatidic acid phosphatase, and a transcription termination sequence capable of terminating transcription in a plant cell, wherein said phosphatidic acid phosphatase encoded by said DNA structural gene includes an amino acid fragment having at least 70% sequence identity to SEQ ID NO: 2.

7. A plant cell comprising a heterologous DNA construct that comprises, as operably linked in the 5' to 3' direction of transcription, a transcriptional initiation region functional in a plant cell, a DNA structural gene sequence encoding a plant phosphatidic acid phosphatase, and a transcription termination sequence capable of terminating transcription in a plant cell, wherein said phosphatidic acid phosphatase encoded by said DNA structural gene includes an amino acid fragment having at least 70% sequence identity to SEQ ID NO: 2.

8. A plant comprising a cell that comprises a DNA construct comprising, as operably linked in the 5' to 3' direction of transcription, a transcriptional initiation region functional in a plant cell, a DNA structural gene sequence encoding a plant phosphatidic acid phosphatase, and a transcription termination sequence capable of terminating transcription in a plant cell, wherein said phosphatidic acid phosphatase encoded by said DNA structural gene includes an amino acid fragment having at least 70% sequence identity to SEQ ID NO: 2.

9. A method of modifying the lipid composition in a plant cell, said method comprising:

transforming a plant cell with DNA comprising as operably linked in the 5' to 3' direction of transcription, a transcriptional initiation region functional in a plant cell, a DNA structural gene sequence encoding a plant phosphatidic acid phosphatase, and a transcription termination sequence, capable of terminating transcription in a plant cell, wherein said phosphatidic acid phosphatase encoded by said DNA structural gene includes an amino acid fragment having at least 70% sequence identity to SEQ ID NO: 2, and growing said plant cell under conditions where transcription of said plant phosphatidic acid phosphatase is initiated, whereby said lipid composition is modified.

10. A method according to claim 9, wherein said encoding sequence comprises at least a portion of a plant phosphatidic acid phosphatase in an antisense orientation, whereby the transcribed mRNA from said encoding sequence is complementary to the equivalent mRNA transcribed from the endogenous gene, whereby the activity of said phosphatidic acid phosphatase protein in said plant cell is suppressed.

11. A method according to claim 10, wherein the synthesis of triglycerides is suppressed in said plant cell.

12. A method according to claim 9, wherein said phosphatidic acid phosphatase protein encoding sequence is in a sense orientation.

13. A method according to claim 12, wherein said lipid composition is increased.

14. A method of modifying the lipid composition in a plant cell, said method comprising:
transforming a plant cell with DNA comprising as operably linked in the 5' to 3' direction of transcription, a transcriptional initiation region functional in a plant cell, a DNA structural gene sequence encoding a soybean phosphatidic acid phosphatase, and a transcription termination sequence capable of terminating transcription in a plant cell, and
growing said plant cell under conditions where transcription of said soybean phosphatidic acid phosphatase is initiated and where said lipid composition is modified.

15. The method according to claim 14, wherein said soybean phosphatidic acid phosphatase is encoded by a nucleic acid comprising a sequence selected from the group consisting of SEQ ID NOs: 10 and 11.

16. The method according to claim 14, wherein said soybean phosphatidic acid phosphatase comprises an amino acid sequence selected from the group consisting of SEQ ID NOs: 16 and 17.

17. The method according to claim 14, wherein said transcriptional initiation region is selected from the group consisting of nopaline synthase transcriptional initiation region, mannopine synthase transcriptional initiation region, CaMV 19S transcriptional initiation region, CaMV 35S transcriptional initiation region, napin transcriptional initiation region, ACP transcriptional initiation region, SSU transcriptional initiation region, PG transcriptional initiation region, zein transcriptional initiation region, phaseolin E transcriptional initiation region, and double 35S transcriptional initiation region.

18. The method according to claim 14, wherein said transcriptional initiation region is a seed-specific transcriptional initiation region.

19. The method according to claim 18, wherein said seed-specific transcriptional initiation region is selected from the group consisting of ACP transcriptional initiation region and napin transcriptional initiation region.

20. A method of modifying the lipid composition in a plant cell comprising:
transforming a plant cell with DNA comprising as operably linked in the 5' to 3' direction of transcription, a promoter functional in a plant cell, a DNA structural gene sequence encoding a plant phosphatidic acid phosphatase, and a transcription termination sequence capable of terminating transcription in a plant cell, wherein said phosphatidic acid phosphatase encoded by said DNA structural gene includes an amino acid fragment having at least 70% sequence identity to SEQ ID NO: 2, and
growing said plant cell under conditions where transcription of said plant phosphatidic acid phosphatase is initiated and where said lipid composition is modified.

21. The method according to claim 20, wherein said promoter is selected from the group consisting of nopaline synthase promoter, mannopine synthase promoter, CaMV 19S promoter, CaMV 35S promoter, napin promoter, ACP promoter, SSU promoter, PG promoter, zein promoter, phaseolin E promoter, and double 35S promoter.

22. The method according to claim 20, wherein said promoter is a seed-specific promoter.

23. The method according to claim 22, wherein said seed-specific promoter is selected from the group consisting of ACP promoter and napin promoter.

24. A method of modifying the lipid composition in a plant cell comprising:
transforming a plant cell with DNA comprising as operably linked in the 5' to 3' direction of transcription, a promoter functional in a plant cell, a DNA structural gene sequence encoding a soybean phosphatidic acid phosphatase, and a transcription termination sequence capable of terminating transcription in a plant cell, and
growing said plant cell under conditions where transcription of said soybean phosphatidic acid phosphatase is initiated and where said lipid composition is modified.

25. The method according to claim 24, wherein said soybean phosphatidic acid phosphatase is encoded by a nucleic acid comprising a sequence selected from the group consisting of SEQ ID NOs: 10 and 11.

26. The method according to claim 24, wherein said soybean phosphatidic acid phosphatase comprises an amino acid sequence selected from the group consisting of SEQ ID NOs: 16 and 17.

27. The method according to claim 24, wherein said promoter is selected from the group consisting of nopaline synthase promoter, mannopine synthase promoter, CaMV 19S promoter, CaMV 35S promoter, napin promoter, ACP promoter, SSU promoter, PG promoter, zein promoter, phaseolin E promoter, and double 35S promoter.

28. The method according to claim 24, wherein said promoter is a seed-specific promoter.

29. The method according to claim 28, wherein said seed-specific promoter is selected from the group consisting of ACP promoter and napin promoter.

30. A recombinant DNA construct comprising, as operably linked in the 5' to 3' direction of transcription, a transcriptional initiation region functional in a plant cell, a DNA structural gene sequence encoding a soybean phosphatidic acid phosphatase, and a transcription termination sequence capable of terminating transcription in a plant cell, wherein said soybean phosphatidic acid phosphatase encoded by said DNA structural gene includes an amino acid fragment having at least 70% sequence identity to SEQ ID NO: 2.

31. The recombinant DNA construct according to claim 30, wherein said soybean phosphatidic acid phosphatase is encoded by a sequence selected from the group consisting of SEQ ID NOs: 10 and 11.

32. The recombinant DNA construct according to claim 30, wherein said soybean phosphatidic acid phosphatase comprises an amino acid sequence selected from the group consisting of SEQ ID NOs: 16 and 17.

33. The recombinant DNA construct according to claim 30, wherein said transcriptional initiation region is selected from the group consisting of nopaline synthase transcriptional initiation region, mannopine synthase transcriptional initiation region, CaMV 19S transcriptional initiation region, CaMV 35S transcriptional initiation region, napin transcriptional initiation region, ACP transcriptional initiation region, SSU transcriptional initiation region, PG transcriptional initiation region, zein transcriptional initiation region, phaseolin E transcriptional initiation region, and double 35S transcriptional initiation region.

34. The recombinant DNA construct according to claim 30, wherein said transcriptional initiation region is a seed-specific transcriptional initiation region.

35. The recombinant DNA construct according to claim 34, wherein said seed-specific transcriptional initiation region is selected from the group consisting of ACP transcriptional initiation region and napin transcriptional initiation region.

36. A recombinant DNA construct comprising, as operably linked in the 5' to 3' direction of transcription, a promoter functional in a plant cell, a DNA structural gene sequence encoding a soybean phosphatidic acid phosphatase, and a transcription termination sequence capable of terminating transcription in a plant cell, wherein said soybean phosphatidic acid phosphatase encoded by said DNA structural gene includes an amino acid fragment having at least 70% sequence identity to SEQ ID NO: 2.

37. The recombinant DNA construct according to claim 36, wherein said soybean phosphatidic acid phosphatase is encoded by a nucleic acid comprising a sequence selected from the group consisting of SEQ ID NOs: 10 and 11.

38. The recombinant DNA construct according to claim 36, wherein said soybean phosphatidic acid phosphatase comprises an amino acid sequence selected from the group consisting of SEQ ID NOs: 16 and 17.

39. The recombinant DNA construct according to claim 36, wherein said promoter is selected from the group consisting of nopaline synthase promoter, mannopine synthase promoter, CaMV 19S promoter, CaMV 35S promoter, napin promoter, ACP promoter, SSU promoter, PG promoter, zein promoter, phaseolin E promoter, and double 35S promoter.

40. The recombinant DNA construct according to claim 36, wherein said promoter is a seed-specific promoter.

41. The recombinant DNA construct according to claim 40, wherein said seed-specific promoter is a heterologous promoter selected from the group consisting of ACP promoter and napin promoter.

42. A method of increasing fatty acid level in a plant cell comprising:
growing a plant containing said plant cell, wherein said plant cell comprises a DNA construct that comprises as operably linked in the 5' to 3' direction of transcription, a heterologous transcriptional initiation region functional in a plant cell, a DNA structural gene sequence encoding a plant phosphatidic acid phosphatase, and a transcription termination sequence capable of terminating transcription in a plant cell, wherein said phosphatidic acid phosphatase encoded by said DNA structural gene includes an amino acid fragment having at least 70% sequence identity to SEQ ID NO: 2, and
expressing said plant phosphatidic acid phosphatase, wherein said fatty acid level is increased.

43. The method according to claim 42 wherein said plant phosphatidic acid phosphatase is overexpressed.

44. The method according to claim 42, wherein said heterologous transcriptional initiation region is selected from the group consisting of nopaline synthase transcriptional initiation region, mannopine synthase transcriptional initiation region, CaMV 19S transcriptional initiation region, CaMV 35S transcriptional initiation region, napin transcriptional initiation region, ACP transcriptional initiation region, SSU transcriptional initiation region, PG transcriptional initiation region, zein transcriptional initiation region, phaseolin E transcriptional initiation region, and double 35S transcriptional initiation region.

45. The method according to claim 42, wherein said heterologous transcriptional initiation region is a seed-specific transcriptional initiation region.

46. The method according to claim 42, wherein said seed-specific transcriptional initiation region is selected from the group consisting of ACP transcriptional initiation region and napin transcriptional initiation region.

47. A method of increasing fatty acid level in a plant cell comprising:
growing a plant containing said plant cell, wherein said plant cell comprises a DNA construct that comprises as operably linked in the 5' to 3' direction of transcription, a heterologous transcriptional initiation region functional in a plant cell, a DNA structural gene sequence encoding a soybean phosphatidic acid phosphatase, and a transcription termination sequence capable of terminating transcription in a plant cell, and
expressing said soybean phosphatidic acid phosphatase, wherein said fatty acid level is increased.

48. The method according to claim 47, wherein said plant phosphatidic acid phosphatase is overexpressed.

49. The method according to claim 47, wherein said heterologous transcriptional initiation region is selected from the group consisting of nopaline synthase transcriptional initiation region, mannopine synthase transcriptional initiation region, CaMV 19S transcriptional initiation region, CaMV 35S transcriptional initiation region, napin transcriptional initiation region, ACP transcriptional initiation region, SSU transcriptional initiation region, PG transcriptional initiation region, zein transcriptional initiation region, phaseolin E transcriptional initiation region, and double 35S transcriptional initiation region.

50. The method according to claim 47, wherein said heterologous transcriptional initiation region is a seed-specific transcriptional initiation region.

51. The method according to claim 50, wherein said seed-specific transcriptional initiation region is selected from the group consisting of ACP transcriptional initiation region and napin transcriptional initiation region.

52. A method of increasing fatty acid level in a plant cell comprising:
growing a plant containing said plant cell, wherein said plant cell comprises a DNA construct that comprises as operably linked in the 5' to 3' direction of transcription, a transcriptional initiation region functional in a plant cell, a heterologous DNA structural gene sequence encoding a plant phosphatidic acid phosphatase, and a transcription termination sequence capable of terminating transcription in a plant cell, wherein said phosphatidic acid phosphatase encoded by said DNA structural gene includes an amino acid fragment having at least 70% sequence identity to SEQ ID NO: 2, and
expressing said plant phosphatidic acid phosphatase, wherein said fatty acid level is increased.

53. The method according to claim 52, wherein said plant phosphatidic acid phosphate is overexpressed.

54. A method of increasing fatty acid level in a plant cell comprising:
growing a plant containing said plant cell, wherein said plant cell comprises a DNA construct that comprises as operably linked in the 5' to 3' direction of transcription, a transcriptional initiation region functional in a plant cell, a heterologous DNA structural gene sequence encoding a soybean phosphatidic acid phosphatase, and a transcription termination sequence capable of terminating transcription in a plant cell, and
expressing said soybean phosphatidic acid phosphatase, wherein said fatty acid level is increased.

55. The method according to claim 54, wherein said soybean phosphatidic acid phosphatase is overexpressed.

56. The method according to claim 54, wherein said soybean phosphatidic acid phosphatase is encoded by a nucleic acid comprising a sequence selected from the group consisting of SEQ ID NOs: 10 and 11.

57. The method according to claim 54, wherein said soybean phosphatidic acid phosphatase comprises an amino acid sequence selected from the group consisting of SEQ ID NOs: 16 and 17.

58. A method of increasing fatty acid level in a plant cell comprising:

growing a plant containing said plant cell, wherein said plant cell comprises a DNA construct that comprises as operably linked in the 5' to 3' direction of transcription, a heterologous promoter functional in a plant cell, a DNA structural gene sequence encoding a plant phosphatidic acid phosphatase, and a transcription termination sequence capable of terminating transcription in a plant cell, wherein said phosphatidic acid phosphatase encoded by said DNA structural gene includes an amino acid fragment having at least 70% sequence identity to SEQ ID NO: 2, and expressing said plant phosphatidic acid phosphatase, wherein said fatty acid level is increased.

59. The method according to claim 58, wherein said plant phosphatidic acid phosphatase is overexpressed.

60. The method according to claim 58, wherein said heterologous promoter is selected from the group consisting of nopaline synthase promoter, mannopine synthase promoter, CaMV 19S promoter, CaMV 35S promoter, napin promoter, ACP promoter, SSU promoter, PG promoter, zein promoter, phaseolin E promoter, and double 35S promoter.

61. The method according to claim 58, wherein said heterologous promoter is a seed-specific promoter.

62. The method according to claim 61, wherein said seed-specific promoter is selected from the group consisting of ACP promoter and napin promoter.

63. A method of increasing fatty acid level in a plant cell comprising:

growing a plant containing said plant cell, wherein said plant cell comprises a DNA construct that comprises as operably linked in the 5' to 3' direction of transcription, a heterologous promoter functional in a plant cell, a DNA structural gene sequence encoding a soybean phosphatidic acid phosphatase, and a transcription termination sequence capable of terminating transcription in a plant cell, and expressing said soybean phosphatidic acid phosphatase, wherein said fatty acid level is increased.

64. The method according to claim 63, wherein said soybean phosphatidic acid phosphatase is overexpressed.

65. The method according to claim 63, wherein said heterologous promoter is selected from the group consisting of nopaline synthase promoter, mannopine synthase promoter, CaMV 19S promoter, CaMV 35S promoter, napin promoter, ACP promoter, SSU promoter, PG promoter, zein promoter, phaseolin E promoter, and double 35S promoter.

66. The method according to claim 63, wherein said heterologous promoter is a seed-specific promoter.

67. The method according to claim 66, wherein said seed-specific promoter is selected from the group consisting of ACP promoter and napin promoter.

68. A method of increasing fatty acid level in a plant cell comprising:

growing a plant containing said plant cell, wherein said plant cell comprises a DNA construct that comprises as operably linked in the 5' to 3' direction of transcription, a promoter functional in a plant cell, a heterologous DNA structural gene sequence encoding a plant phosphatidic acid phosphatase, and a transcription termination sequence capable of terminating transcription in a plant cell, wherein said phosphatidic acid phosphatase encoded by said DNA structural gene includes an amino acid fragment having at least 70% sequence identity to SEQ ID NO: 2, and expressing said plant phosphatidic acid phosphatase, wherein said fatty acid level is increased.

69. The method according to claim 68, wherein said plant phosphatidic acid phosphatase is overexpressed.

70. A method of increasing fatty acid level in a plant cell comprising:

growing a plant containing said plant cell, wherein said plant cell comprises a DNA construct that comprises as operably linked in the 5' to 3' direction of transcription, a promoter functional in a plant cell, a heterologous DNA structural gene sequence encoding a soybean phosphatidic acid phosphatase, and a transcription termination sequence capable of terminating transcription in a plant cell, and expressing said soybean phosphatidic acid phosphatase, wherein said fatty acid level is increased.

71. The method according to claim 70, wherein said plant phosphatidic acid phosphatase is overexpressed.

72. The method according to claim 70, wherein said soybean phosphatidic acid phosphatase is encoded by a nucleic acid comprising a sequence selected from the group consisting of SEQ ID NOs: 10 and 11.

73. The method according to claim 70, wherein said soybean phosphatidic acid phosphatase comprises an amino acid sequence selected from the group consisting of SEQ ID NOs: 16 and 17.

74. An isolated DNA sequence encoding a soybean phosphatidic acid phosphatase, wherein said soybean phosphatidic acid phosphatase comprises an amino acid sequence selected from the group consisting of: SEQ ID NOs: 16 and 17.

\* \* \* \* \*

SEQUENCE LISTING

```
<160> NUMBER OF SEQ ID NOS:  55

<210> SEQ ID NO 1
<211> LENGTH: 19
<212> TYPE: PRT
<213> ORGANISM: Unknown
<220> FEATURE:
<221> NAME/KEY: misc_feature
<222> LOCATION: ()..()
<223> OTHER INFORMATION: Conserved peptide sequence
<221> NAME/KEY: misc_feature
<222> LOCATION: ()..()
<223> OTHER INFORMATION: Xaa at positions 6,7,17, and 18 is unknown

<400> SEQUENCE: 1

Thr Asp Ile Ala Lys Xaa Xaa Ile Gly Arg Leu Arg Pro His Phe Leu
1               5                   10                  15

Xaa Xaa Cys

<210> SEQ ID NO 2
<211> LENGTH: 14
<212> TYPE: PRT
<213> ORGANISM: Unknown
<220> FEATURE:
<221> NAME/KEY: misc_feature
<222> LOCATION: ()..()
<223> OTHER INFORMATION: Conserved peptide sequence

<400> SEQUENCE: 2

Leu Ser Arg Val Ser Asp Tyr Lys His His Trp Ser Asp Val
1               5                   10

<210> SEQ ID NO 3
<211> LENGTH: 1232
<212> TYPE: DNA
```

<213> ORGANISM: Arabidopsis sp.

<400> SEQUENCE: 3

| | | | | | |
|---|---|---|---|---|---|
| caaaaaactt | tatctttcct | tcctttgaaa | tctcccggag | aaaaactata | gagattttcc | 60 |
| gtttcccgct | ttaatacagt | gccccaattc | gcgcgacaca | tagagtgtag | agacgctttc | 120 |
| acgagcgttt | ccgacgtcgg | actttcagct | catcatctcc | acatctttaa | cggtaaagat | 180 |
| taatcatgcc | tgaaattcat | ttgggtgctc | atacaataag | atcccatgga | gtaacagtcg | 240 |
| cgaggttcca | catgcatgac | tggctcattc | ttctgctgct | aatagtcatt | gaaattgttc | 300 |
| ttaatgtcat | cgaacccttt | catcgttttg | ttggagaaga | tatgctcact | gatctcagat | 360 |
| accctctgca | ggacaacaca | attccttcct | gggctgtccc | gttgatagct | gttgtgctac | 420 |
| cttttgctgt | catttgtgtt | tactacttca | ttagaaatga | tgtttatgac | ctgcatcatg | 480 |
| caatactagg | gcttttgttc | tctgtactta | taaccggtgt | cataaccgat | gctataaagg | 540 |
| acgctgttgg | tcgacctcgt | cctgatttct | tttggcgttg | tttccctgac | ggtatatggga | 600 |
| tctttcacaa | tgtcacgaag | aatgttctat | gtactggagc | taaggatgtg | gtcaaagagg | 660 |
| gacacaagag | cttcccagc | ggccacacat | cttggtcgtt | tgctggtcta | ggatttctat | 720 |
| cgttatactt | gtctgggaaa | atcagggtgt | ttgaccagag | agggcatgtt | gcaaagctct | 780 |
| gcattgtgat | tttacctcta | ctggttgcag | cattggttgg | tgtatccaga | gttgatgact | 840 |
| attggcatca | ctggcaagat | gttttttggag | gagctatcat | aggattgact | gtggccacat | 900 |
| tttgttatct | gcaattttc | cctcctccat | acgatccaga | cggttgggga | cctcatgcct | 960 |
| acttccagat | gctggcagac | tcaagaaatg | atgtccaaga | ttcagcagga | atgaatcatc | 1020 |
| taagcgtgag | gcaaacagag | ctagagagcg | tacgttgatg | gagaagagac | gtccatggaa | 1080 |
| atatcaagaa | gcaacacgcg | ggacaccacc | cgtatgcttc | agaaccgcta | agtgaagtct | 1140 |
| ttgtactcgt | tatctatcaa | tcttaggcat | tgtcgcattg | atatgtattg | gcttaatcac | 1200 |
| aaggcccaat | attggttgga | agcccattcg | ct | | | 1232 |

<210> SEQ ID NO 4
<211> LENGTH: 35
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic oligonucleotide

<400> SEQUENCE: 4
ccagatctgc atgctcaacg tacgctctct agctc         35

<210> SEQ ID NO 5
<211> LENGTH: 38
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic oligonucleotide

<400> SEQUENCE: 5
ccagatctct cgagacaatg cctgaaattc atttgggt      38

<210> SEQ ID NO 6
<211> LENGTH: 254
<212> TYPE: DNA
<213> ORGANISM: Brassica napus

<400> SEQUENCE: 6

```
tgatatgcca tggtgataaa agtgtcataa gtgaagggca caaaagcttc ccaagcggac      60
acacctcttg gtcttttgcg ggtctaggat tcttgtcgct gtatttatca gggaagattc     120
aagcgtttca tggtaaaggc cacgttgcga acgtatgcat tgtcatactc cctttgcatg     180
ttgcagctct tgtcggattt ccgtgtagat gactatggca ttcactggca gacgctttgc     240
tggaggctgc tagg                                                        254
```

<210> SEQ ID NO 7
<211> LENGTH: 1222
<212> TYPE: DNA
<213> ORGANISM: Arabidopsis sp.

<400> SEQUENCE: 7

```
cccacgcgtc cgcccacattt ctctttaacc tcatctcatc tcttagtcga gatcttcact     60
ttctgatgac aatagggtcg ttttctctt ctctcttatt ctggcgcaat tctcaggacc      120
aggaggcgca gagagggagg atgcaggaga tagatcttag tgttcacact ataaagtccc     180
atggaggaag agtcgcttct aaacacaagc acgattggat catactcgtc atcttgattg     240
ccatcgagat aggcttgaac ctcatctctc ctttctaccg ctacgtggga aaagacatga     300
tgactgacct caagtacccct tcaaggaca acaccgtacc tatctggtct gtccctgtgt     360
acgctgtgct tcttcccatc atagtgttcg tctgcttcta cctgaagagg acatgtgtgt     420
acgatctgca ccacagcatc ctcgggctgc tcttcgccgt cttgataact ggtgtcatca     480
ctgactccat caaggtagcc accggacgcc ctcgtcctaa cttctactgg cgctgcttcc     540
ccgacggcaa agagctgtat gatgcgttgg gaggtgtggt atgccacggc aaggcagctg     600
aggtcaagga aggccacaag agcttcccga gcggacacac ttcctggtcc tttgcggggc     660
ttacattcct ttcccttac ctctctggca aaatcaaggc cttcaacaat gaaggacatg     720
tggcgaaact ctgcctcgtg atcttccctc tgcttgccgc ttgtcttgtg gggatatctc     780
gtgtggatga ctactggcac cactggcaag atgtcttcgc aggagctctc attggcaccc     840
ttgtagccgc cttctgctac cgtcagttct accccaaccc ttaccacgaa gaaggatggg     900
gtccctacgc ctatttcaag gcagctcaag aacgaggagt ccctgtgacc tcctcccaaa     960
acggagatgc cttgagggct atgtctctgc agatggattc aacatctctc gaaaacatgg    1020
aatctggcac ttccaccgct cccagatgat cctcctctct tattatttga ttcattattt    1080
ggttttttcat tttgatttgg ccgtcgtcgt gagattgtga atggtgtagc tacatactgt    1140
atgtgtattc aaaactctac ttgtaccatt acattttgt aaatccactc ttcatgaaat    1200
tgacgttaaa aaaaaaaaa aa                                              1222
```

<210> SEQ ID NO 8
<211> LENGTH: 1113
<212> TYPE: DNA
<213> ORGANISM: Arabidopsis sp.

<400> SEQUENCE: 8

```
gcgtccgatc gactagagtc tgcacaggat gagagaggca cagctaggcg gtcacactct      60
gaggtcccat ggaatgactg ttgcaaggac tcacatgcat gattggatca ttctcgtgtt     120
acttgttatt ctcgagtgtg tactccttat aatccaccca ttttatcgct tgttggtaa     180
agatatgatg actgatctaa gttacccgtt aaagagtaac accgtaccaa tttggtctgt     240
```

-continued

```
cccggtatat gcgatgctgt tacctttggt aatcttcatc tttatctact tccgtcgaag    300
agatgtttat gatcttcatc acgcggtgct aggtctctta tactctgttc tggtgacagc    360
agtacttacc gatgcaataa agaatgcagt tggtcgacca cgtcctgact tcttctggcg    420 ttgtttttcca gatggcaaag ctctttatga tagccttgga gatgttatat gccatggtga    480
taaaagcgtc ataagggaag gtcacaaaag ctttccaagt ggacacacgt catggtcttt    540
ttcgggtctc ggatttcttt cgctttactt atcgggaaag attcaagcat tgacggtaa    600 aggccacgtt gcaaagctat gcatagtcat actcccttg ctatttgcag ctcttgtcgg    660
catttcccgt gttgatgact attggcatca ttggcaagac gtctttgcag gaggcttgct    720
aggtcttgcg atctctacaa tctgttatct tcaattttc ccgccaccat atcacaccga    780
aggttgggga ccatatgctt acttccaagt gttggaggct gcgagagtgc aaggagcagc    840
gaatggagca gtgcagcagc cgccgcccca agttaacaac ggtgaagaag aagacggtgg    900
gtttatgggt ttacatttgg tggataatcc gactatgagg agagaagagg atgtagaaac    960
tggtagaggc tgagatgaag aaactctgaa gctggtttgg ttacttgtta ggacacttc    1020 tcttgttctt ttgattcttt gttggacaac tttagtagat ttctctaaga taactaatag    1080
agtcgtttgg tttaaaaaa aaaaaaaaaa aaa    1113
```

<210> SEQ ID NO 9
<211> LENGTH: 1389
<212> TYPE: DNA
<213> ORGANISM: Zea mays

<400> SEQUENCE: 9

```
gtcgacccac gcgtccgccc acgcgtccgc ggacgcgtgg gcgctagcag cggcggcgcc     60
ggcagttggt agccgcgacc gagacacggc gggtgacctg ccccgccgca gtcgggtgt    120 atgtattacc accgccagaa ttccaggaga caatggcaga ccagttaggg tcttacacta    180
ttagatccca tggaatgata ttggcaaggt tgcacatgta tgactggata atacttctcc    240
tccttgctgt catagacggg ctgttgaata taattgaacc atttcaccgt tttgttggga    300
aagacatgat gactgacttg agatatccta tgaagggcaa tacagtgcca ttttgggctg    360
ttccactgat tggaattata ctgccttggg ccatctttgt tgggatttac ttcaaaaaga    420
agaattttta tgatttgcac catggcatac tggggattct atactcagtg ctgataactg    480
cagtgattac tgatgcaatt aaggatggtg ttggacggcc tcgtccagat ttttctggc    540 gctgtttccc taatggaaat gatgtttatg ataacattac tactggtgtt atatgcaatg    600
gagtgaagag cgtaatcaag gaaggccaca agagctttcc cagtggacac agttcatggt    660
cttttgctgg tctaggcttc cttgcatggt acttagctgg gaaactcaca gcctttgacc    720
gcaaagggca tattgcgaag ctatgcattg tgttcctgcc tctccttact gccgcacttg    780
tggctgtttc tcgagtggac gactactggc atcattggca agatgtattt gcaggggtc    840 ttataggtct tacagttgct tcgttttgct acctacagtt ttttcccatat cctttcgatg    900 gcgatgcttt gtggcctcac gcatacgcgg tccggttagc cgaggagggg aacagcagaa    960
atgcgaactc gtacagcgtg agaccaaccg agatcgaaac agtcgatatt cctgggcacg   1020
gtgcgatcat cacctaaga gagactctaa acgatgtgga gtctggcagt gccaggagat   1080
tgtgagatgg gtctgcaggt gtggagattg atgtctcaga taccatggga gttgcttgca   1140
tatgtgtaca ggtagatcta ttgtagagct gttgactgct gccaccgtga taggggaggg   1200
ttgcttagac gggcctggca gtaaatttac ttggtagggg tgctgtttct tctgagaacc   1260
```

```
tttggctttt gtttgtatat atactcttat caaagtgttt gctgacactt ttgtaaccag   1320
tttggtcgct gcattcagca actatgatca aaaaaaaaaa aaaaaaaaaa aaaaaaaag   1380 ggcggccgc                                                          1389

<210> SEQ ID NO 10
<211> LENGTH: 1364
<212> TYPE: DNA
<213> ORGANISM: Glycine sp.

<400> SEQUENCE: 10
ctcgagttga tattcccaat ctctctgttt ctatttcttt gttcgttgct tcacactatg     60
gcttcttggt gggatttaag acccttcttt cgttttcagt ctgttaggac ccgatttcag    120
gaattcagga cgagggaagt ccaacttggt tcacatactg tgagttctca tggatatgca    180
gttgcaagaa cacacaaaca tgattggctc attctcttgc tcctcgtgtt gattgttatc    240
agcctgtaca ttatccatcc tttccatcgc tttgttggga aggatatgat gactgatctc    300
aaatatccac tgaagagtaa tacagttcct gcttgggcta ttcctatata tgcaatttta    360
ttgcccatag tgatctttct tggtgtctac atccgaagga gagacgtcta tgatcttcat    420
catgctgtgc tgggtttatt gttctccgtt ttaataacag cagtatttac tgaggcaata    480
aaaaatgcag taggtcgacc tcgaccagac ttcttctggc gatgttttcc agatggaaag    540
gatgtttatg ataaatgggg agatgtcatt tgtcatggtg accaaaaggt cataaaggaa    600
ggatacaaga gtttcccaag tggtcatact tcagggtcat tttctggtct gggtttttta    660
tcattgtact tatctggaaa aataaaaagca tttgatcgca aggtcatgt tgcaaaactt    720 tgcattgttt ttctaccact acttgttgca tcacttgttg catttctcg agttgatgac    780 tactggcacc actggcaaga cgtgtttgcg ggaggtcttt tagggcttac agtggctaca    840
ttttgctatt tgcagttttt tcctcctcct tatcattctg aaggctgggg tccttatgcg    900
tattttagga tgttggaaga atctcgtggt atgacccaag ttcctagtgt tcaaaattct    960
ggtcaagcgc agttagcaga ggctcaggct gagagccaag aggaacaagg tctccacggg   1020
tgtatggggt taactttatc acgggatcat catgcagcat tgaatgactg tgaatctggg   1080 agggataaa gtctgtacat ttcatgatct tgctctctgt aaaatgtaaa tcagatgtta   1140
gttcgtagcc taggatttta accagtattt aaaactaaca cattttgttg aatagttgtt   1200
tctattcagt cactagtgtc tctgaaaact ttgaagcgta gttgtttgta agagtcaggt   1260
ttgggacaat taacctttgt tatttcaata ttttgtgaat atgttgacat aagaaaatac   1320
gaaatctctt gagaagattg ccgttcattc aaaaaaaaaa aaaa                    1364

<210> SEQ ID NO 11
<211> LENGTH: 1276
<212> TYPE: DNA
<213> ORGANISM: Glycine sp.

<400> SEQUENCE: 11
ctcgagcctc gaatctcgtg cacgtgccgt tgcagcaaaa aatgccagaa attcagttgg     60
gtatgcatac tatcagatca catggaacta gagtggcaag acacatatg cacgactggt    120 tgattctttt gcttcttgtg atcatcgatg ctgtcttgaa tttaatacag ccatttcacc    180
gttttgttgg agaggggatg atgacagacc ttagataccc attgaaagct aatacaattc    240
ccttttgggc tgttccgata atagcaatat tgttaccact ggctgttttt ctcgtttact    300
```

-continued

```
atttcattcg taaggatgtc tatgacctcc accatgctat aatgggcctt ctatttctg      360
tactcattac tgcggtgatg actgatgcta tcaaggatgc tgttggacgg ccaaggccag     420
acttcttctg gcgttgtttc cctgatgaa aagggggtgtt tgatccagta acaagtaatg     480
ttctgtgtac tggagataag ggtgttatta aggaagggca caaaagtttc cccagtggac     540
atacctcttg gtcctttgct ggtcttgttt atcttgcttg gtatctatct ggaaaactta     600
gggcatttga ccgcaggggg catgttgcaa agctctgtct tgttttctta ccaatcctcg     660
tggcagctat gattgctgtc tctcgtgttg atgattactg gcatcattgg caagatgtgt     720
ttgctggagc tcttataggg atgataattg cttcattttg ttacttacaa ttcttttccac    780
ctccatatga cgtagatggt tgggaccctc atgcatattt ccagatgttg gctgaatctc     840
gtaatggtgc tcagccctct actgtcaata atgagattca tcatgtccaa tctgctgagc     900
ttcaggctgt atctttgtat atcccacctc aacatgatgc agatacacga ggcaatagct     960
gggattcaag ccccatgtta ggtgcatccc aaaatgtaag aacacactga cgacatagga    1020
aagatcacca acatgtccat aatctgtaaa aattatagga gggattcgtt gcagataaac    1080
cactttagca ttgttggtgg tttaaaatgc ggatatcaat caatttcttt gcttgttgga    1140
ttggaaattt gggatgccat gttagttgtc tttaattttc cggccagctt atatttgtta    1200
gttgtcaaag cactgtttct atacagagaa tgatttaatc ggctcaacag gattcaagca    1260
aaaaaaaaaa aaaaaa                                                   1276
```

<210> SEQ ID NO 12
<211> LENGTH: 290
<212> TYPE: PRT
<213> ORGANISM: Arabidopsis sp.

<400> SEQUENCE: 12

```
Met Pro Glu Ile His Leu Gly Ala His Thr Ile Arg Ser His Gly Val
 1               5                  10                  15

Thr Val Ala Arg Phe His Met His Asp Trp Leu Ile Leu Leu Leu
            20                  25                  30

Ile Val Ile Glu Ile Val Leu Asn Val Ile Glu Pro Phe His Arg Phe
        35                  40                  45

Val Gly Glu Asp Met Leu Thr Asp Leu Arg Tyr Pro Leu Gln Asp Asn
    50                  55                  60

Thr Ile Pro Phe Trp Ala Val Pro Leu Ile Ala Val Leu Pro Phe
65                  70                  75                  80

Ala Val Ile Cys Val Tyr Tyr Phe Ile Arg Asn Asp Val Tyr Asp Leu
                85                  90                  95

His His Ala Ile Leu Gly Leu Leu Phe Ser Val Leu Ile Thr Gly Val
            100                 105                 110

Ile Thr Asp Ala Ile Lys Asp Ala Val Gly Arg Pro Arg Pro Asp Phe
        115                 120                 125

Phe Trp Arg Cys Phe Pro Asp Gly Ile Gly Ile Phe His Asn Val Thr
    130                 135                 140

Lys Asn Val Leu Cys Thr Gly Ala Lys Asp Val Val Lys Glu Gly His
145                 150                 155                 160

Lys Ser Phe Pro Ser Gly His Thr Ser Trp Ser Phe Ala Gly Leu Gly
                165                 170                 175

Phe Leu Ser Leu Tyr Leu Ser Gly Lys Ile Arg Val Phe Asp Gln Arg
            180                 185                 190

Gly His Val Ala Lys Leu Cys Ile Val Ile Leu Pro Leu Leu Val Ala
```

```
            195                 200                 205
Ala Leu Val Gly Val Ser Arg Val Asp Asp Tyr Trp His His Trp Gln
    210                 215                 220

Asp Val Phe Gly Gly Ala Ile Ile Gly Leu Thr Val Ala Thr Phe Cys
225                 230                 235                 240

Tyr Leu Gln Phe Phe Pro Pro Tyr Asp Pro Asp Gly Trp Gly Pro
                245                 250                 255

His Ala Tyr Phe Gln Met Leu Ala Asp Ser Arg Asn Asp Val Gln Asp
                260                 265                 270

Ser Ala Gly Met Asn His Leu Ser Val Arg Gln Thr Glu Leu Glu Ser
                275                 280                 285

Val Arg
    290

<210> SEQ ID NO 13
<211> LENGTH: 348
<212> TYPE: PRT
<213> ORGANISM: Arabidopsis sp.

<400> SEQUENCE: 13

His Ala Ser Ala Thr Phe Leu Phe Asn Leu Ile Ser Ser Leu Ser Arg
1               5                   10                  15

Asp Leu His Phe Leu Met Thr Ile Gly Ser Phe Ser Ser Leu Leu
                20                  25                  30

Phe Trp Arg Asn Ser Gln Asp Gln Glu Ala Gln Arg Gly Arg Met Gln
            35                  40                  45

Glu Ile Asp Leu Ser Val His Thr Ile Lys Ser His Gly Gly Arg Val
50                  55                  60

Ala Ser Lys His Lys His Asp Trp Ile Ile Leu Val Ile Leu Ile Ala
65                  70                  75                  80

Ile Glu Ile Gly Leu Asn Leu Ile Ser Pro Phe Tyr Arg Tyr Val Gly
                85                  90                  95

Lys Asp Met Met Thr Asp Leu Lys Tyr Pro Phe Lys Asp Asn Thr Val
                100                 105                 110

Pro Ile Trp Ser Val Pro Val Tyr Ala Val Leu Leu Pro Ile Ile Val
            115                 120                 125

Phe Val Cys Phe Tyr Leu Lys Arg Thr Cys Val Tyr Asp Leu His His
130                 135                 140

Ser Ile Leu Gly Leu Leu Phe Ala Val Leu Ile Thr Gly Val Ile Thr
145                 150                 155                 160

Asp Ser Ile Lys Val Ala Thr Gly Arg Pro Arg Pro Asn Phe Tyr Trp
                165                 170                 175

Arg Cys Phe Pro Asp Gly Lys Glu Leu Tyr Asp Ala Leu Gly Gly Val
                180                 185                 190

Val Cys His Gly Lys Ala Ala Glu Val Lys Glu Gly His Lys Ser Phe
            195                 200                 205

Pro Ser Gly His Thr Ser Trp Ser Phe Ala Gly Leu Thr Phe Leu Ser
    210                 215                 220

Leu Tyr Leu Ser Gly Lys Ile Lys Ala Phe Asn Asn Glu Gly His Val
225                 230                 235                 240

Ala Lys Leu Cys Leu Val Ile Phe Pro Leu Leu Ala Ala Cys Leu Val
                245                 250                 255

Gly Ile Ser Arg Val Asp Asp Tyr Trp His His Trp Gln Asp Val Phe
                260                 265                 270
```

Ala Gly Ala Leu Ile Gly Thr Leu Val Ala Ala Phe Cys Tyr Arg Gln
              275                 280                 285

Phe Tyr Pro Asn Pro Tyr His Glu Glu Gly Trp Gly Pro Tyr Ala Tyr
        290                 295                 300

Phe Lys Ala Ala Gln Glu Arg Gly Val Pro Val Thr Ser Ser Gln Asn
305                 310                 315                 320

Gly Asp Ala Leu Arg Ala Met Ser Leu Gln Met Asp Ser Thr Ser Leu
                325                 330                 335

Glu Asn Met Glu Ser Gly Thr Ser Thr Ala Pro Arg
            340                 345

<210> SEQ ID NO 14
<211> LENGTH: 314
<212> TYPE: PRT
<213> ORGANISM: Arabidopsis sp.

<400> SEQUENCE: 14

Met Arg Glu Ala Gln Leu Gly Gly His Thr Leu Arg Ser His Gly Met
1               5                   10                  15

Thr Val Ala Arg Thr His Met His Asp Trp Ile Ile Leu Val Leu Leu
            20                  25                  30

Val Ile Leu Glu Cys Val Leu Leu Ile Ile His Pro Phe Tyr Arg Phe
        35                  40                  45

Val Gly Lys Asp Met Met Thr Asp Leu Ser Tyr Pro Leu Lys Ser Asn
    50                  55                  60

Thr Val Pro Ile Trp Ser Val Pro Val Tyr Ala Met Leu Leu Pro Leu
65                  70                  75                  80

Val Ile Phe Ile Phe Ile Tyr Phe Arg Arg Arg Asp Val Tyr Asp Leu
                85                  90                  95

His His Ala Val Leu Gly Leu Leu Tyr Ser Val Leu Val Thr Ala Val
            100                 105                 110

Leu Thr Asp Ala Ile Lys Asn Ala Val Gly Arg Pro Arg Pro Asp Phe
        115                 120                 125

Phe Trp Arg Cys Phe Pro Asp Gly Lys Ala Leu Tyr Asp Ser Leu Gly
    130                 135                 140

Asp Val Ile Cys His Gly Asp Lys Ser Val Ile Arg Glu Gly His Lys
145                 150                 155                 160

Ser Phe Pro Ser Gly His Thr Ser Trp Ser Phe Ser Gly Leu Gly Phe
                165                 170                 175

Leu Ser Leu Tyr Leu Ser Gly Lys Ile Gln Ala Phe Asp Gly Lys Gly
            180                 185                 190

His Val Ala Lys Leu Cys Ile Val Ile Leu Pro Leu Leu Phe Ala Ala
        195                 200                 205

Leu Val Gly Ile Ser Arg Val Asp Asp Tyr Trp His His Trp Gln Asp
    210                 215                 220

Val Phe Ala Gly Gly Leu Leu Gly Leu Ala Ile Ser Thr Ile Cys Tyr
225                 230                 235                 240

Leu Gln Phe Phe Pro Pro Pro Tyr His Thr Glu Gly Trp Gly Pro Tyr
                245                 250                 255

Ala Tyr Phe Gln Val Leu Glu Ala Ala Arg Val Gln Gly Ala Ala Asn
            260                 265                 270

Gly Ala Val Gln Gln Pro Pro Gln Val Asn Asn Gly Glu Glu Glu
        275                 280                 285

Asp Gly Gly Phe Met Gly Leu His Leu Val Asp Asn Pro Thr Met Arg
    290                 295                 300

```
Arg Glu Glu Asp Val Glu Thr Gly Arg Gly
305             310

<210> SEQ ID NO 15
<211> LENGTH: 310
<212> TYPE: PRT
<213> ORGANISM: Zea mays

<400> SEQUENCE: 15

Met Ala Asp Gln Leu Gly Ser Tyr Thr Ile Arg Ser His Gly Met Ile
1               5                   10                  15

Leu Ala Arg Leu His Met Tyr Asp Trp Ile Ile Leu Leu Leu Leu Ala
                20                  25                  30

Val Ile Asp Gly Leu Leu Asn Ile Ile Glu Pro Phe His Arg Phe Val
            35                  40                  45

Gly Lys Asp Met Met Thr Asp Leu Arg Tyr Pro Met Lys Gly Asn Thr
        50                  55                  60

Val Pro Phe Trp Ala Val Pro Leu Ile Gly Ile Leu Pro Trp Ala
65                  70                  75                  80

Ile Phe Val Gly Ile Tyr Phe Lys Lys Lys Asn Phe Tyr Asp Leu His
                85                  90                  95

His Gly Ile Leu Gly Ile Leu Tyr Ser Val Leu Ile Thr Ala Val Ile
            100                 105                 110

Thr Asp Ala Ile Lys Asp Gly Val Gly Arg Pro Arg Pro Asp Phe Phe
        115                 120                 125

Trp Arg Cys Phe Pro Asn Gly Asn Asp Val Tyr Asp Asn Ile Thr Thr
    130                 135                 140

Gly Val Ile Cys Asn Gly Val Lys Ser Val Ile Lys Glu Gly His Lys
145                 150                 155                 160

Ser Phe Pro Ser Gly His Ser Ser Trp Ser Phe Ala Gly Leu Gly Phe
                165                 170                 175

Leu Ala Trp Tyr Leu Ala Gly Lys Leu Thr Ala Phe Asp Arg Lys Gly
            180                 185                 190

His Ile Ala Lys Leu Cys Ile Val Phe Leu Pro Leu Leu Thr Ala Ala
        195                 200                 205

Leu Val Ala Val Ser Arg Val Asp Tyr Trp His His Trp Gln Asp
    210                 215                 220

Val Phe Ala Gly Gly Leu Ile Gly Leu Thr Val Ala Ser Phe Cys Tyr
225                 230                 235                 240

Leu Gln Phe Phe Pro Tyr Pro Phe Asp Gly Asp Ala Leu Trp Pro His
                245                 250                 255

Ala Tyr Ala Val Arg Leu Ala Glu Glu Gly Asn Ser Arg Asn Ala Asn
            260                 265                 270

Ser Tyr Ser Val Arg Pro Thr Glu Ile Glu Thr Val Asp Ile Pro Gly
        275                 280                 285

His Gly Ala Ile Ile Thr Leu Arg Glu Thr Leu Asn Asp Val Glu Ser
    290                 295                 300

Gly Ser Ala Arg Arg Leu
305             310

<210> SEQ ID NO 16
<211> LENGTH: 322
<212> TYPE: PRT
<213> ORGANISM: Glycine sp.

<400> SEQUENCE: 16
```

Met Pro Glu Ile Gln Leu Gly Met His Thr Ile Arg Ser His Gly Thr
1               5                   10                  15

Arg Val Ala Arg Thr His Met His Asp Trp Leu Ile Leu Leu Leu Leu
            20                  25                  30

Val Ile Ile Asp Ala Val Leu Asn Leu Ile Gln Pro Phe His Arg Phe
        35                  40                  45

Val Gly Glu Gly Met Met Thr Asp Leu Arg Tyr Pro Leu Lys Ala Asn
    50                  55                  60

Thr Ile Pro Phe Trp Ala Val Pro Ile Ile Ala Ile Leu Leu Pro Leu
65                  70                  75                  80

Ala Val Phe Leu Val Tyr Tyr Phe Ile Arg Lys Asp Val Tyr Asp Leu
                85                  90                  95

His His Ala Ile Met Gly Leu Leu Phe Ser Val Leu Ile Thr Ala Val
            100                 105                 110

Met Thr Asp Ala Ile Lys Asp Ala Val Gly Arg Pro Arg Pro Asp Phe
        115                 120                 125

Phe Trp Arg Cys Phe Pro Asp Gly Lys Gly Val Phe Asp Pro Val Thr
    130                 135                 140

Ser Asn Val Leu Cys Thr Gly Asp Lys Gly Val Ile Lys Glu Gly His
145                 150                 155                 160

Lys Ser Phe Pro Ser Gly His Thr Ser Trp Ser Phe Ala Gly Leu Val
                165                 170                 175

Tyr Leu Ala Trp Tyr Leu Ser Gly Lys Leu Arg Ala Phe Asp Arg Arg
            180                 185                 190

Gly His Val Ala Lys Leu Cys Leu Val Phe Leu Pro Ile Leu Val Ala
        195                 200                 205

Ala Met Ile Ala Val Ser Arg Val Asp Asp Tyr Trp His His Trp Gln
210                 215                 220

Asp Val Phe Ala Gly Ala Leu Ile Gly Met Ile Ile Ala Ser Phe Cys
225                 230                 235                 240

Tyr Leu Gln Phe Phe Pro Pro Tyr Asp Val Asp Gly Trp Gly Pro
                245                 250                 255

His Ala Tyr Phe Gln Met Leu Ala Glu Ser Arg Asn Gly Ala Gln Pro
            260                 265                 270

Ser Thr Val Asn Asn Glu Ile His His Val Gln Ser Ala Glu Leu Gln
        275                 280                 285

Ala Val Ser Leu Tyr Ile Pro Pro Gln His Asp Ala Asp Thr Arg Gly
    290                 295                 300

Asn Ser Trp Asp Ser Ser Pro Met Leu Gly Ala Ser Gln Asn Val Arg
305                 310                 315                 320

Thr His

<210> SEQ ID NO 17
<211> LENGTH: 343
<212> TYPE: PRT
<213> ORGANISM: Glycine sp.

<400> SEQUENCE: 17

Met Ala Ser Trp Trp Asp Leu Arg Pro Phe Phe Arg Phe Gln Ser Val
1               5                   10                  15

Arg Thr Arg Phe Gln Glu Phe Arg Thr Arg Glu Val Gln Leu Gly Ser
            20                  25                  30

His Thr Val Ser Ser His Gly Tyr Ala Val Ala Arg Thr His Lys His
        35                  40                  45

Asp Trp Leu Ile Leu Leu Leu Val Leu Ile Val Ile Ser Leu Tyr
    50                  55                  60

Ile Ile His Pro Phe His Arg Phe Val Gly Lys Asp Met Met Thr Asp
65                  70                  75                  80

Leu Lys Tyr Pro Leu Lys Ser Asn Thr Val Pro Ala Trp Ala Ile Pro
                85                  90                  95

Ile Tyr Ala Ile Leu Leu Pro Ile Val Ile Phe Leu Gly Val Tyr Ile
            100                 105                 110

Arg Arg Arg Asp Val Tyr Asp Leu His His Ala Val Leu Gly Leu Leu
        115                 120                 125

Phe Ser Val Leu Ile Thr Ala Val Phe Thr Glu Ala Ile Lys Asn Ala
    130                 135                 140

Val Gly Arg Pro Arg Pro Asp Phe Phe Trp Arg Cys Phe Pro Asp Gly
145                 150                 155                 160

Lys Asp Val Tyr Asp Lys Trp Gly Asp Val Ile Cys His Gly Asp Gln
                165                 170                 175

Lys Val Ile Lys Glu Gly Tyr Lys Ser Phe Pro Ser Gly His Thr Ser
            180                 185                 190

Gly Ser Phe Ser Gly Leu Gly Phe Leu Ser Leu Tyr Leu Ser Gly Lys
        195                 200                 205

Ile Lys Ala Phe Asp Arg Lys Gly His Val Ala Lys Leu Cys Ile Val
    210                 215                 220

Phe Leu Pro Leu Leu Val Ala Ser Leu Val Gly Ile Ser Arg Val Asp
225                 230                 235                 240

Asp Tyr Trp His His Trp Gln Asp Val Phe Ala Gly Gly Leu Leu Gly
                245                 250                 255

Leu Thr Val Ala Thr Phe Cys Tyr Leu Gln Phe Phe Pro Pro Pro Tyr
            260                 265                 270

His Ser Glu Gly Trp Gly Pro Tyr Ala Tyr Phe Arg Met Leu Glu Glu
        275                 280                 285

Ser Arg Gly Met Thr Gln Val Pro Ser Val Gln Asn Ser Gly Gln Ala
    290                 295                 300

Gln Leu Ala Glu Ala Gln Ala Glu Ser Gln Glu Gln Gly Leu His
305                 310                 315                 320

Gly Cys Met Gly Leu Thr Leu Ser Arg Asp His His Ala Ala Leu Asn
            325                 330                 335

Asp Cys Glu Ser Gly Arg Gly
            340

<210> SEQ ID NO 18
<211> LENGTH: 267
<212> TYPE: DNA
<213> ORGANISM: Zea mays
<220> FEATURE:
<221> NAME/KEY: misc_feature
<222> LOCATION: (1)..(267)
<223> OTHER INFORMATION: n = A, T, C, or G

<400> SEQUENCE: 18
ctcagtgctc ataactgcag tgattactga tgcaattaag gatggtgttg gacggcctcg     60
tccagatttt ttctggcgct gtttccctga tggaaatgat gtttatgata acatcactac    120
tggtgttata tgcaatggag tgaagagtgt aatcaaggaa ggccacaaga gctttcccag    180
tggacacact tcatgcttcc ttgcatggta cttagctggg anactcacgg cttttgatcg    240
naaaggacct attgcgaact atgcatt                                         267

<210> SEQ ID NO 19
<211> LENGTH: 293
<212> TYPE: DNA
<213> ORGANISM: Zea mays

<400> SEQUENCE: 19

```
accgacttga gttatcccct caagggcaac acaatcccat tttgggctgt tccactgatt      60
gcgatcgtgc taccctttggt tatctttgct gtcatttact tcaaaaagaa aaatgtctat    120
gatttacacc acggcatact aggtatcttg tattcagtgc ttataactgc tgtgatcact    180
gatgcaatta aggatggtgt tggtcgccct cggccagatt tcttttggcg ttgttttcct    240
gatggcaaac ctaattttaa taatataacc caccgatgtg atatggccat gga           293
```

<210> SEQ ID NO 20
<211> LENGTH: 288
<212> TYPE: DNA
<213> ORGANISM: Zea mays
<220> FEATURE:
<221> NAME/KEY: misc_feature
<222> LOCATION: (1)..(288)
<223> OTHER INFORMATION: n = A, T, C, or G

<400> SEQUENCE: 20

```
cgcttagcag cggcggcgcc ggcagttggt agccgcgacc gagacacggc gggtgacctg      60
ccccgncgca gtcggggtgn atgtantacc ancgccagaa tancaggaga caatggcaga    120
ccagttaggg tcttacacta ttagatccca tggaatgata ttggcaaggt tgcacatgta    180
tgactggata atacttctcc tccttgctgt catagacggg ctgttgaata taattgaacc    240
atttcaccgt tttgttggga aagacatgat gactgacttg agatatcc                 288
```

<210> SEQ ID NO 21
<211> LENGTH: 227
<212> TYPE: DNA
<213> ORGANISM: Zea mays

<400> SEQUENCE: 21

```
cttagtggca gtttctcgag ttgatgacta ttggcatcat tggcaagacg tatgtactgg      60
cggattactt gggttcacgg ttgcttccat ttgctacctg cagttttttc cactaccatc    120
tgatgaaaat ggactgtggc cgcacgcata tttccgacac attcttgagc cagagggtga    180
cagccaagcg caacccacgt acatgagccg tcgcagctcg gttcaga                  227
```

<210> SEQ ID NO 22
<211> LENGTH: 222
<212> TYPE: DNA
<213> ORGANISM: Zea mays

<400> SEQUENCE: 22

```
tgctgtcata gacgggctgt tgaatataat tgaaccattt caccgttttg ttgggaaaga      60
catgatgact gacttgagat atcctatgaa gggcaataca gtgccatttt gggctgttcc    120
actgattgga attatactgc cttgggccat cttttgttggg atttacttca aaagaagaa    180 tttttatgat ttgcaccatg gcatactggg gattctatac tc                      222
```

<210> SEQ ID NO 23
<211> LENGTH: 233
<212> TYPE: DNA
<213> ORGANISM: Zea mays
<220> FEATURE:

<210> SEQ ID NO 23 (continued)
<221> NAME/KEY: misc_feature
<222> LOCATION: (1)..(233)
<223> OTHER INFORMATION: n = A, T, C, or G

<400> SEQUENCE: 23
cacagccttt gaccgcaaag ggcatattgc gaantattgc attgtgttcc tgcctctccn      60
nnctgcngca cttgtggctg ttatctcgag tggacgacta ctggcatcat tggcaagatg     120
tatttgcagg gggtcttata ggtcttacag ttgcttcgtt ttgctaccta cagttttcc     180 catatccttt cgatggcgat gctttgtggc ctcacgcata cgcggtccgg tta            233

<210> SEQ ID NO 24
<211> LENGTH: 259
<212> TYPE: DNA
<213> ORGANISM: Zea mays
<220> FEATURE:
<221> NAME/KEY: misc_feature
<222> LOCATION: (1)..(259)
<223> OTHER INFORMATION: n = A, T, C, or G

<400> SEQUENCE: 24
attaaggatg gtgttggacg gcctcgtcca gatttttct ggcgctgttt ccctaatgga      60
aatgatgttt atgataacat tactactggt gttatatgca atggagtgaa gagcgtaatc    120
aaggaaggcc acaagagctt tcccagtgga cacagttcat ggtcttttgc tggtctaggc    180
ttccttgcat ggtacttagc tgggaaactc acagcctttg accgcaaagg gcatattgcg    240
aantatgcat tgtgttcct                                                  259

<210> SEQ ID NO 25
<211> LENGTH: 262
<212> TYPE: DNA
<213> ORGANISM: Zea mays

<400> SEQUENCE: 25
cccagtggac acagttcatg gtcttttgct ggtctaggct tccttgcatg gtacttagct      60
gggaaactca cagcctttga ccgcaaaggg catattgcga actatgcatt gtgttcctgc    120
ctctccttac tgccgcactt gtggctgttt ctcgagtgga cgactactgg catcattggc    180
aagatgtatt tgcaggggt cttataggtc ttacagttgc ttcgttttgc tacctacagt    240
ttttcccata tcctttcgat gg                                              262

<210> SEQ ID NO 26
<211> LENGTH: 256
<212> TYPE: DNA
<213> ORGANISM: Zea mays

<400> SEQUENCE: 26
aactgcagtg attactgatg caattaagga tggtgttgga cggcctcgtc cagatttttt      60
ctggcgctgt ttccctaatg gaaatgatgt ttatgataac attactactg gtgttatatg    120
caatggagtg aagagcgtaa tcaaggaagg ccacaagagc tttcccagtg gacacagttc    180
atggtctttt gctggtctag gcttccttgc atggtactta gctgggaaac tcacagcctt    240
tgaccgcaaa gggcat                                                     256

<210> SEQ ID NO 27
<211> LENGTH: 289
<212> TYPE: DNA
<213> ORGANISM: Zea mays
<220> FEATURE:
<221> NAME/KEY: misc_feature
<222> LOCATION: (1)..(289)
<223> OTHER INFORMATION: n = A, T, C, or G

<400> SEQUENCE: 27
gataactgca gtgattactg atgcaattaa ggatggtgtt ggacggcctc gtccagattt      60
tttctggcgc tgtttcccta atggaaatga tgtttatgat aacattacta ctggtgttat     120
atgcaatgga gtgaagagcg taatcaagga aggccacaag agctttccca gtggacacag     180
ttcatggtct tttgctggtc taggctcctt gcatggtact tagctgggaa actcacagcc     240
ttgnaccgca aagggcatat tgcgaantat gcatgtgttc ctgccctcc                 289

<210> SEQ ID NO 28
<211> LENGTH: 272
<212> TYPE: DNA
<213> ORGANISM: Zea mays
<220> FEATURE:
<221> NAME/KEY: misc_feature
<222> LOCATION: (1)..(272)
<223> OTHER INFORMATION: n = A, T, C, or G

<400> SEQUENCE: 28
cnttgnnggg canccccgggc agnnaccang ttnnacnnga cgcggctgcc gtacgtggcc     60
ctcgntatgc tctgcgtgtt gctggctgga ntgccttttg taattcttac ttcaaggcat    120
acccncttcc aacgangagt attctgnaat gntgagtccn tcangtaccc ttacaaagaa    180
gacacnatnc cttatgcgtt attaggtggn atnatcannc cattcaggat tatcggtatt    240
anncgtggng naacctgtcc gtatatgtaa cc                                   272

<210> SEQ ID NO 29
<211> LENGTH: 297
<212> TYPE: DNA
<213> ORGANISM: Zea mays

<400> SEQUENCE: 29
gaaggccaca agagctttcc cagtggacac acttcatggt cttttgctgg tctaggcttc      60
cttgcatggt acttagctgg gaaactcacg gcttttgatc gcaaaggaca tattcggaag    120
ctatgcattg tgtttctgcc tcttcttact gctgcgcttg tggctgtttc tcgagtggat    180
gactactggc atcattggca agatgtattt gcaggggggtc ttataggtct tacagttgct    240
tcattttgct atctacagtt ttttccatat ccttttgatg gcgagctttg tggcctc        297

<210> SEQ ID NO 30
<211> LENGTH: 288
<212> TYPE: DNA
<213> ORGANISM: Zea mays
<220> FEATURE:
<221> NAME/KEY: misc_feature
<222> LOCATION: (1)..(288)
<223> OTHER INFORMATION: n = A, T, C, or G

<400> SEQUENCE: 30
gaaggccaca agagctttcc cagtggacac acttcatggt cttatgctgg tctaggcttc      60
cttgcatggt acttagctng gaaactcacg gcttttgatc gcaaaggaca tattcggaag    120
ctatgcattg tgattntgcc tcttcttact gctgcgcttg tggctnnttc tcgagtggat    180
gactactggc atcattggca agatgtattt acaggggggtc ttataggtct taanttgctt    240
catggtgcta tctacagtnt ttccatatcc tttgatggcg atgctttg                   288

<210> SEQ ID NO 31

<211> LENGTH: 281
<212> TYPE: DNA
<213> ORGANISM: Zea mays
<220> FEATURE:
<221> NAME/KEY: misc_feature
<222> LOCATION: (1)..(281)
<223> OTHER INFORMATION: n = A, T, C, or G

<400> SEQUENCE: 31

```
gaaggccaca agagctttcc cagtggacac acttcatggt cttttgctgg tctaggcttc      60
cttgcatggt acttagctgg gaaactcacg gcttttgatc gcaaaggaca tattcggaag     120
ctatgcattg tgtttctgcc tcttcttact gctgcgcttg tggctgtttc tcgagtggat     180
gactactggc atcattggca agatgtattt gcaggggggtc ttataggtct tacagttgct     240
tcatttgcng nnctacagtt ttttccatat cctttgatgg c                         281
```

<210> SEQ ID NO 32
<211> LENGTH: 279
<212> TYPE: DNA
<213> ORGANISM: Zea mays
<220> FEATURE:
<221> NAME/KEY: misc_feature
<222> LOCATION: (1)..(279)
<223> OTHER INFORMATION: n = A, T, C, or G

<400> SEQUENCE: 32

```
gnaggccaca agagctttcc cagtggnnac acttcatggt cttttgctgg tctaggcttc      60
cttgcatggn acttagctgg gatnctcacg gcttttganc gcaaaggaca tattcggaag     120
ctatcattgt gtttctgnct cttcttactg ctgcgcttgt ggcngttnct cgagtngntg     180
actactggca tcnttggcaa gatgtanttc cangggtct natangncta nagttgcttc     240
antctgntan ctacagttnt ntccatatcc ntntgatgg                            279
```

<210> SEQ ID NO 33
<211> LENGTH: 294
<212> TYPE: DNA
<213> ORGANISM: Zea mays

<400> SEQUENCE: 33

```
ggacatgttg caaaagtctg cattgtcctt tcccctctgc ttcttgcagc cttagtggca      60
gtttctcgag ttgatgacta ttggcatcat tggcaagacg tatgtactgg cggattactt     120
gggttcacgg ttgcttccat ttgctacctg cagttttttt ccactaccat ctgatgaaaa     180
tggactgtgg ccgcacgcat atttccgaca cattcttgag ccagagggtg acagccaagc     240
gcaacccacg tacatgagcc gtcgcagctc ggttcagaac ggttccttca gtac           294
```

<210> SEQ ID NO 34
<211> LENGTH: 345
<212> TYPE: DNA
<213> ORGANISM: Zea mays
<220> FEATURE:
<221> NAME/KEY: misc_feature
<222> LOCATION: ()..()
<223> OTHER INFORMATION: n = A, T, C, or G

<400> SEQUENCE: 34

```
ctactggtgt tatatgcaat ggagtgaaga gcgtaatcaa ggaaggccac aagagctttc      60
ccantggaca cagttcatgg tcttttgctg gtctaggctt ccttgcatgg tacttagctg     120
ggaanctcac agcctttgac cgcaaagggc atattgcgaa ntatgcattg tgttcctgcc     180
tctccttact gccgcacttg tggctgtttc tcgagtggac gactactggc atcattggca     240
```
agatgtattt gcaggggtc ttataggtct tacagttgct tcgttttgct acctacagtt      300
tttcccatat ccttntcgat ggcgatgctt tgtggcctca cgcaa                     345

<210> SEQ ID NO 35
<211> LENGTH: 260
<212> TYPE: DNA
<213> ORGANISM: Zea mays
<220> FEATURE:
<221> NAME/KEY: misc_feature
<222> LOCATION: (1)..(260)
<223> OTHER INFORMATION: n = A, T, C, or G

<400> SEQUENCE: 35
tgcncctncc tctccttact gccgcacttg tngctgtttc tcgagtgtgn cgactactga      60
ncatcattgn tcaatatgta ngatgcaggg ggtcgtatac gtcttacagt tgcttcgttn     120
ngctacctan agtgtntccc atatcctctn gatggcgatg nttngtngnc tnangcatac     180
ncggtccggt nngccgagga tgggaacagn agtaatgcga actcgtacag cgtnanaccn     240
nccnagatct atnacagtng                                                260

<210> SEQ ID NO 36
<211> LENGTH: 310
<212> TYPE: DNA
<213> ORGANISM: Zea mays
<220> FEATURE:
<221> NAME/KEY: misc_feature
<222> LOCATION: (1)..(310)
<223> OTHER INFORMATION: n = A, T, C, or G

<400> SEQUENCE: 36
gtggctgntt ctcgagttga tgattactgg catcactggc aagangtcta tgccggcgga      60
tcataggnct aacagtngct tcattctgtt acctgcagtt cttcccatat ccctttgaca     120
atgatgccct atggccacac gcatactnct cnaagctagc tgagacacac agtaatggta     180
atgcaaactc aatcaacata agacctacag agtntgaaga tgaaccagat gaccatggtg     240 cattttcct gagggacacc agccctatct tggagtcaat ggagtctggc aggagaccat     300 gaagnnnnnt                                                          310

<210> SEQ ID NO 37
<211> LENGTH: 275
<212> TYPE: DNA
<213> ORGANISM: Zea mays

<400> SEQUENCE: 37
aattccagga gacgacgagg cgccgatccg tagcggcgcc gagggcgata tcgaggagcc      60
gctggtctca cgccgcaccg agacaatggc agaccagtta gggtcttaca caattagatc     120
ccatggaatg atattggcaa gattacacat gtatgactgg ataatacttc tcctccttgc     180
tgtcatagac gggctgttga atataattga accatttcac cgttttgttg gaaaagacat     240
gatgaccgac ttgagatatc ctatgaaggg caata                                275

<210> SEQ ID NO 38
<211> LENGTH: 407
<212> TYPE: DNA
<213> ORGANISM: Brassica napus

<400> SEQUENCE: 38
gcttggggac catatgctta cttccttgtg ttggaggcgg cacgagctca agctcaagct      60

```
caagctcaag ctcaagcagc agagaatgaa gcggcccaac gaccgcctca gggtgataac      120
ggtgaagagg aagacggtgg gtttatggga ctacatttgg tggataatcc gagtatgagg      180
agagaagaag cagatgtaga agctggtaga gtgccgtcta aaagctgaga ttataaagaa      240
tcactgaagc tggtttggtt gcagcttaag acacttttgc cttgttctta tacattcttt      300
tgtttgccta cttgtccttt ggtgtttggt ttacagttta atgcctttaa tttgttcaat      360
tcagttttgt tcaaaaaaaa aaaagagggg aaggagaag gagagag                     407
```

<210> SEQ ID NO 39
<211> LENGTH: 38
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 39

```
ggatccgcgg ccgcagaaat gcaggagata gatcttag                              38
```

<210> SEQ ID NO 40
<211> LENGTH: 34
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 40

```
cctgcaggaa gctttcatct gggagcggtg gaag                                  34
```

<210> SEQ ID NO 41
<211> LENGTH: 44
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 41

```
gagctcctgc aggaagcttt cagcctctac cagtttctac atcc                       44
```

<210> SEQ ID NO 42
<211> LENGTH: 39
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 42

```
ggatccgcgg ccgcacagga tgagagaggc acagctagg                             39
```

<210> SEQ ID NO 43
<211> LENGTH: 56
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 43
cgcgatttaa atggcgcgcc ctgcaggcgg ccgcctgcag ggcgcgccat ttaaat        56

<210> SEQ ID NO 44
<211> LENGTH: 32
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 44
tcgaggatcc gcggccgcaa gcttcctgca gg                                  32

<210> SEQ ID NO 45
<211> LENGTH: 32
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 45
tcgacctgca ggaagcttgc ggccgcggat cc                                  32

<210> SEQ ID NO 46
<211> LENGTH: 36
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 46
tcgaggatcc gcggccgcaa gcttcctgca ggagct                              36

<210> SEQ ID NO 47
<211> LENGTH: 28
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 47
cctgcaggaa gcttgcggcc gcggatcc                                       28

<210> SEQ ID NO 48
<211> LENGTH: 36
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 48
tcgacctgca ggaagcttgc ggccgcggat ccagct                              36

<210> SEQ ID NO 49
<211> LENGTH: 28
<212> TYPE: DNA
<213> ORGANISM: Artificial/Unknown
<220> FEATURE:

```
<221> NAME/KEY: misc_feature
<222> LOCATION: ()..()
<223> OTHER INFORMATION: Synthetic Oligonucleotide

<400> SEQUENCE: 49
ggatccgcgg ccgcaagctt cctgcagg                                              28

<210> SEQ ID NO 50
<211> LENGTH: 39
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 50
gatcacctgc aggaagcttg cggccgcgga tccaatgca                                  39

<210> SEQ ID NO 51
<211> LENGTH: 31
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic Oligonucleotide

<400> SEQUENCE: 51
ttggatccgc ggccgcaagc ttcctgcagg t                                          31

<210> SEQ ID NO 52
<211> LENGTH: 289
<212> TYPE: PRT
<213> ORGANISM: Saccharomyces cerevisiae

<400> SEQUENCE: 52

Met Asn Arg Val Ser Phe Ile Lys Thr Pro Phe Asn Ile Gly Ala Lys
1               5                   10                  15

Trp Arg Leu Glu Asp Val Phe Leu Leu Ile Ile Met Ile Leu Leu Asn
            20                  25                  30

Tyr Pro Val Tyr Tyr Gln Gln Pro Phe Glu Arg Gln Phe Tyr Ile Asn
        35                  40                  45

Asp Leu Thr Ile Ser His Pro Tyr Ala Thr Thr Glu Arg Val Asn Asn
    50                  55                  60

Asn Met Leu Phe Val Tyr Ser Phe Val Val Pro Ser Leu Thr Ile Leu
65                  70                  75                  80

Ile Ile Gly Ser Ile Leu Ala Asp Arg Arg His Leu Ile Phe Ile Leu
                85                  90                  95

Tyr Thr Ser Leu Leu Gly Leu Ser Leu Ala Trp Phe Ser Thr Ser Phe
            100                 105                 110

Phe Thr Asn Phe Ile Lys Asn Trp Ile Gly Arg Leu Arg Pro Asp Phe
        115                 120                 125

Leu Asp Arg Cys Gln Pro Val Glu Gly Leu Pro Leu Asp Thr Leu Phe
    130                 135                 140

Thr Ala Lys Asp Val Cys Thr Thr Lys Asn His Glu Arg Leu Leu Asp
145                 150                 155                 160

Gly Phe Arg Thr Thr Pro Ser Gly His Ser Ser Glu Ser Phe Ala Gly
                165                 170                 175

Leu Gly Tyr Leu Tyr Phe Trp Leu Cys Gly Gln Leu Leu Thr Glu Ser
            180                 185                 190
```

```
Pro Leu Met Pro Leu Trp Arg Lys Met Val Ala Phe Leu Pro Leu Leu
            195                 200                 205

Gly Ala Ala Leu Ile Ala Leu Ser Arg Thr Gln Asp Tyr Arg His His
        210                 215                 220

Phe Val Asp Val Ile Leu Gly Ser Met Leu Gly Tyr Ile Met Ala His
225                 230                 235                 240

Phe Phe Tyr Arg Arg Ile Phe Pro Pro Ile Asp Asp Pro Leu Pro Phe
                245                 250                 255

Lys Pro Leu Met Asp Asp Ser Asp Val Thr Leu Glu Glu Ala Val Thr
            260                 265                 270

His Gln Arg Ile Pro Asp Glu Glu Leu His Pro Leu Ser Asp Glu Gly
        275                 280                 285

Met

<210> SEQ ID NO 53
<211> LENGTH: 283
<212> TYPE: PRT
<213> ORGANISM: Mus musculus

<400> SEQUENCE: 53

Met Phe Asp Lys Thr Arg Leu Pro Tyr Val Ala Leu Asp Val Ile Cys
1               5                   10                  15

Val Leu Leu Ala Gly Leu Pro Phe Ala Ile Leu Thr Ser Arg His Thr
            20                  25                  30

Pro Phe Gln Arg Gly Ile Phe Cys Asn Asp Asp Ser Ile Lys Tyr Pro
        35                  40                  45

Tyr Lys Glu Asp Thr Ile Pro Tyr Ala Leu Leu Gly Gly Ile Val Ile
    50                  55                  60

Pro Phe Cys Ile Ile Val Met Ser Ile Gly Glu Ser Leu Ser Val Tyr
65                  70                  75                  80

Phe Asn Val Leu His Ser Asn Ser Phe Val Gly Asn Pro Tyr Ile Ala
                85                  90                  95

Thr Ile Tyr Lys Ala Val Gly Ala Phe Leu Phe Gly Val Ser Ala Ser
            100                 105                 110

Gln Ser Leu Thr Asp Ile Ala Lys Tyr Thr Ile Gly Ser Leu Arg Pro
        115                 120                 125

His Phe Leu Ala Ile Cys Asn Pro Asp Trp Ser Lys Ile Asn Cys Ser
    130                 135                 140

Asp Gly Tyr Ile Glu Asp Tyr Ile Cys Gln Gly Asn Glu Glu Lys Val
145                 150                 155                 160

Lys Glu Gly Arg Leu Ser Phe Tyr Ser Gly His Ser Ser Phe Ser Met
                165                 170                 175

Tyr Cys Met Leu Phe Val Ala Leu Tyr Leu Gln Ala Arg Met Lys Gly
            180                 185                 190

Asp Trp Ala Arg Leu Leu Arg Pro Met Leu Gln Phe Gly Leu Ile Ala
        195                 200                 205

Phe Ser Ile Tyr Val Gly Leu Ser Arg Val Ser Asp Tyr Lys His His
    210                 215                 220

Trp Ser Asp Val Thr Val Gly Leu Ile Gln Gly Ala Ala Met Ala Ile
225                 230                 235                 240

Leu Val Ala Leu Tyr Val Ser Asp Phe Phe Lys Asp Thr His Ser Tyr
                245                 250                 255

Lys Glu Arg Lys Glu Glu Asp Pro His Thr Thr Leu His Glu Thr Ala
            260                 265                 270
```

Ser Ser Arg Asn Tyr Ser Thr Asn His Glu Pro
            275                 280

<210> SEQ ID NO 54
<211> LENGTH: 282
<212> TYPE: PRT
<213> ORGANISM: Rattus sp.

<400> SEQUENCE: 54

Met Phe Asp Lys Pro Arg Leu Pro Tyr Val Leu Asp Val Ile Cys
1               5                   10                  15

Val Leu Leu Ala Gly Leu Pro Phe Ile Ile Leu Thr Ser Arg His Thr
            20                  25                  30

Pro Phe Gln Arg Gly Val Phe Cys Thr Asp Glu Ser Ile Lys Tyr Pro
        35                  40                  45

Tyr Arg Glu Asp Thr Ile Pro Tyr Ala Leu Leu Gly Gly Ile Val Ile
    50                  55                  60

Pro Phe Cys Ile Ile Val Met Ile Thr Gly Glu Thr Leu Ser Val Tyr
65                  70                  75                  80

Phe Asn Val Leu His Ser Asn Ser Phe Val Ser Asn His Tyr Ile Ala
                85                  90                  95

Thr Ile Tyr Lys Ala Val Gly Ala Phe Leu Phe Gly Ala Ser Ala Ser
            100                 105                 110

Gln Ser Leu Thr Asp Ile Ala Lys Tyr Ser Ile Gly Arg Leu Arg Pro
        115                 120                 125

His Phe Leu Ala Val Cys Asn Pro Asp Trp Ser Lys Ile Asn Cys Ser
    130                 135                 140

Asp Gly Tyr Ile Glu Asn Phe Val Cys Gln Gly Asn Glu Gln Lys Val
145                 150                 155                 160

Arg Glu Gly Arg Leu Ser Phe Tyr Ser Gly His Ser Ser Phe Ser Met
                165                 170                 175

Tyr Cys Met Leu Phe Val Ala Leu Tyr Leu Gln Ala Arg Met Lys Gly
            180                 185                 190

Asp Trp Ala Arg Leu Leu Arg Pro Met Leu Gln Phe Gly Leu Val Ala
        195                 200                 205

Leu Ser Ile Tyr Val Gly Leu Ser Arg Val Ser Asp Tyr Lys His His
    210                 215                 220

Trp Ser Asp Val Leu Ile Gly Leu Ile Gln Gly Ala Val Val Ala Ile
225                 230                 235                 240

Leu Val Val Leu Tyr Val Thr Asp Phe Phe Lys Thr Thr Glu Ser Asn
                245                 250                 255

Lys Glu Arg Lys Glu Asp Ser His Thr Thr Leu His Glu Thr Thr Asn
            260                 265                 270

Arg Gln Ser Tyr Ala Arg Asn His Glu Pro
        275                 280

<210> SEQ ID NO 55
<211> LENGTH: 233
<212> TYPE: PRT
<213> ORGANISM: Homo sapiens

<400> SEQUENCE: 55

Met Gln Asn Tyr Lys Tyr Asp Lys Ala Ile Val Pro Glu Ser Lys Asn
1               5                   10                  15

Gly Gly Ser Pro Ala Leu Asn Asn Pro Arg Arg Ser Gly Ser Lys
            20                  25                  30

-continued

```
Arg Val Leu Leu Ile Cys Leu Asp Leu Phe Cys Leu Phe Met Ala Gly
         35                  40                  45

Leu Pro Phe Leu Ile Ile Glu Thr Ser Thr Ile Lys Pro Tyr His Arg
         50                  55                  60

Gly Phe Tyr Cys Asn Asp Glu Ser Ile Lys Tyr Pro Leu Lys Thr Gly
 65                  70                  75                  80

Glu Thr Ile Asn Asp Ala Val Leu Cys Ala Val Gly Ile Val Ile Ala
                 85                  90                  95

Ile Leu Ala Ile Ile Thr Gly Glu Phe Tyr Arg Ile Tyr Tyr Leu Lys
             100                 105                 110

Lys Ser Arg Ser Thr Ile Gln Asn Pro Tyr Val Ala Ala Leu Tyr Lys
             115                 120                 125

Gln Val Gly Cys Phe Leu Phe Gly Cys Ala Ile Ser Gln Ser Phe Thr
         130                 135                 140

Asp Ile Ala Lys Val Ser Ile Gly Arg Leu Arg Pro His Phe Leu Ser
145                 150                 155                 160

Val Cys Asn Pro Asp Phe Ser Gln Ile Asn Cys Ser Glu Gly Tyr Ile
                165                 170                 175

Gln Asn Tyr Arg Cys Arg Gly Asp Asp Ser Lys Val Gln Glu Ala Arg
             180                 185                 190

Lys Ser Phe Phe Ser Gly His Ala Ser Phe Ser Met Tyr Thr Met Leu
         195                 200                 205

Tyr Leu Val Leu Tyr Leu Gln Ala Arg Phe Thr Trp Arg Gly Ala Arg
         210                 215                 220

Cys Ser Gly Pro Ser Cys Ser Ser Pro
225                 230
```